(12) United States Patent
Parker et al.

(10) Patent No.: US 9,040,909 B2
(45) Date of Patent: *May 26, 2015

(54) SYSTEM AND METHOD FOR SIMULTANEOUS DETECTION OF SECONDARY ELECTRONS AND LIGHT IN A CHARGED PARTICLE BEAM SYSTEM

(71) Applicant: FEI Company, Hillsboro, OR (US)

(72) Inventors: N. William Parker, Hillsboro, OR (US); Mark W. Utlaut, Scappoose, OR (US)

(73) Assignee: FEI Company, Hillsboro, OR (US)

( * ) Notice: Subject to any disclaimer, the term of this patent is extended or adjusted under 35 U.S.C. 154(b) by 37 days.

This patent is subject to a terminal disclaimer.

(21) Appl. No.: 13/681,746

(22) Filed: Nov. 20, 2012

(65) Prior Publication Data

US 2014/0131573 A1 May 15, 2014

Related U.S. Application Data

(63) Continuation of application No. 13/017,016, filed on Jan. 30, 2011, now Pat. No. 8,319,181.

(51) Int. Cl.
*G01N 23/00* (2006.01)
*G01N 23/225* (2006.01)
*G01N 21/64* (2006.01)
*H01J 37/22* (2006.01)
*H01J 37/28* (2006.01)

(52) U.S. Cl.
CPC .......... *G01N 23/225* (2013.01); *G01N 21/6428* (2013.01); *G01N 21/6458* (2013.01); *H01J 37/228* (2013.01); *H01J 37/28* (2013.01); *H01J 2237/206* (2013.01); *H01J 2237/24455* (2013.01); *H01J 2237/2803* (2013.01)

(58) Field of Classification Search
USPC .................................. 250/305, 306, 307, 311
See application file for complete search history.

(56) References Cited

U.S. PATENT DOCUMENTS

| 4,587,425 A | | 5/1986 | Plows | |
|---|---|---|---|---|
| 4,990,776 A | * | 2/1991 | Fushimi et al. | ............... 250/310 |

(Continued)

FOREIGN PATENT DOCUMENTS

| EP | 1724809 | 11/2006 |
|---|---|---|
| EP | 1739715 | 1/2007 |

(Continued)

*Primary Examiner* — Michael Logie
*Assistant Examiner* — Jason McCormack
(74) *Attorney, Agent, or Firm* — Scheinberg & Associates, PC; Michael O. Scheinberg

(57) ABSTRACT

A method and system for the imaging and localization of fluorescent markers such as fluorescent proteins or quantum dots within biological samples is disclosed. The use of recombinant genetics technology to insert "reporter" genes into many species is well established. In particular, green fluorescent proteins (GFPs) and their genetically-modified variants ranging from blue to yellow, are easily spliced into many genomes at the sites of genes of interest (GoIs), where the GFPs are expressed with no apparent effect on the functioning of the proteins of interest (PoIs) coded for by the GoIs. One goal of biologists is more precise localization of PoIs within cells. The invention is a method and system for enabling more rapid and precise PoI localization using charged particle beam-induced damage to GFPs. Multiple embodiments of systems for implementing the method are presented, along with an image processing method relatively immune to high statistical noise levels.

19 Claims, 21 Drawing Sheets

(56) References Cited

U.S. PATENT DOCUMENTS

| | | | |
|---|---|---|---|
| 5,393,976 A * | 2/1995 | Koike | 250/310 |
| 6,373,070 B1 | 4/2002 | Rasmussen | |
| 6,476,387 B1 * | 11/2002 | Nishimura et al. | 850/9 |
| 6,633,034 B1 * | 10/2003 | Crewe | 850/9 |
| 6,730,907 B1 * | 5/2004 | Feuerbaum et al. | 850/9 |
| 6,916,101 B2 | 7/2005 | Yanagi et al. | |
| 7,317,515 B2 | 1/2008 | Buijsse et al. | |
| 7,668,697 B2 | 2/2010 | Volkov et al. | |
| 8,319,181 B2 * | 11/2012 | Parker et al. | 250/307 |
| 8,497,476 B2 * | 7/2013 | Hatakeyama et al. | 250/310 |
| 2002/0024014 A1 * | 2/2002 | Kazumori | 250/311 |
| 2006/0098188 A1 | 5/2006 | Buijsse et al. | |
| 2007/0161047 A1 | 7/2007 | Zhong et al. | |
| 2008/0185509 A1 * | 8/2008 | Knowles | 250/251 |
| 2008/0274155 A1 | 11/2008 | Barton et al. | |
| 2008/0293096 A1 | 11/2008 | Muller et al. | |
| 2008/0293919 A1 | 11/2008 | Kaplan et al. | |
| 2009/0041753 A1 | 2/2009 | Miller et al. | |
| 2009/0314939 A1 | 12/2009 | Stern et al. | |
| 2010/0140470 A1 * | 6/2010 | Shachal | 250/307 |
| 2012/0193530 A1 * | 8/2012 | Parker et al. | 250/307 |
| 2012/0241608 A1 * | 9/2012 | Shachal | 250/307 |

FOREIGN PATENT DOCUMENTS

| | | |
|---|---|---|
| EP | 1956632 | 8/2008 |
| JP | 2003157789 | 5/2003 |

* cited by examiner

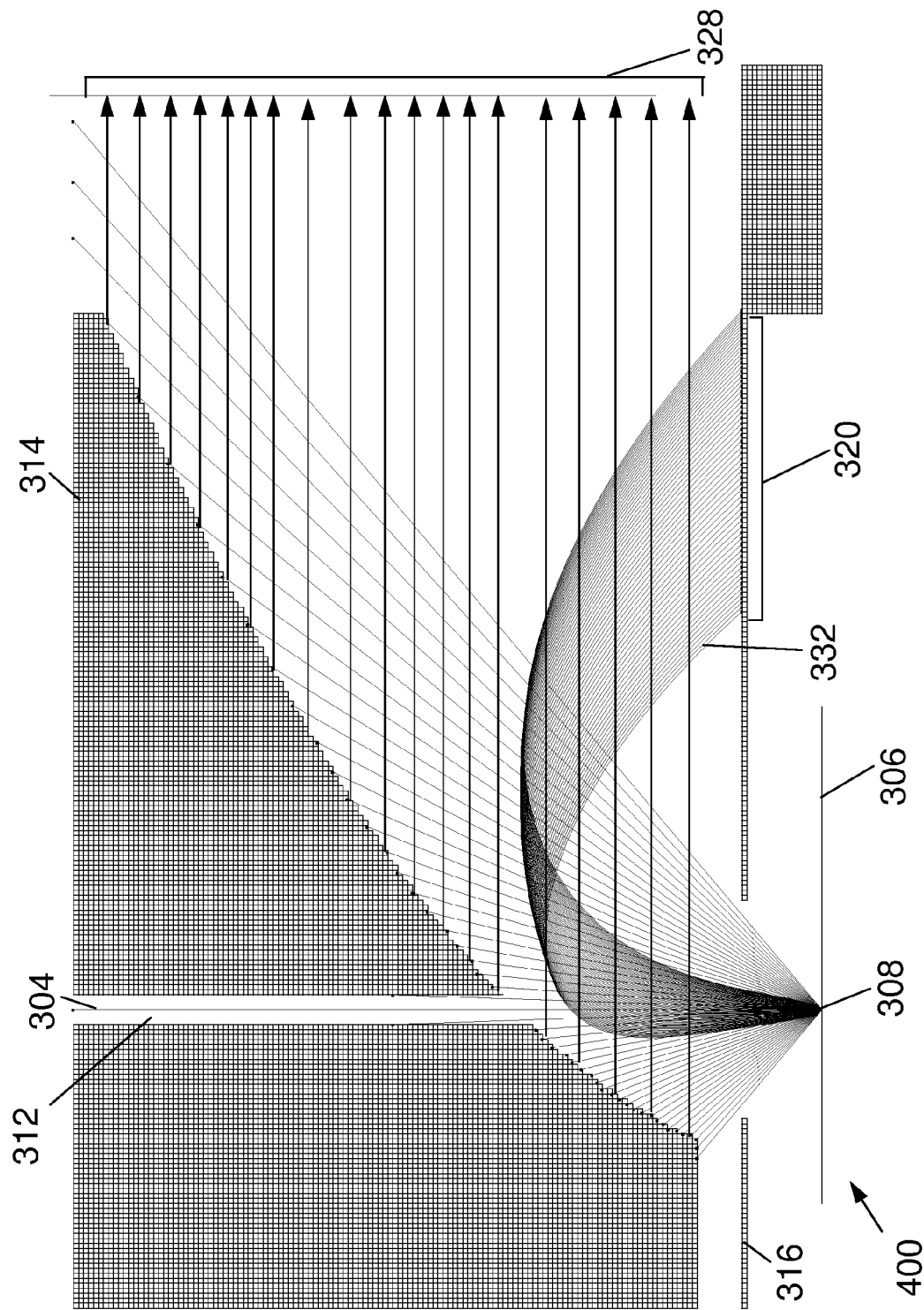

SYSTEM AND METHOD FOR SIMULTANEOUS DETECTION OF SECONDARY ELECTRONS AND LIGHT IN A CHARGED PARTICLE BEAM SYSTEM

The present application is a continuation of U.S. patent application Ser. No. 13/017,016, with a filing date of Jan. 30, 2011, U.S. Pat. No. 8,319,181, which is hereby incorporated by reference.

TECHNICAL FIELD OF THE INVENTION

The present invention relates generally to focused charged particle beam systems and, in particular, to systems used to excite and localize fluorescent markers in a sample.

BACKGROUND OF THE INVENTION

Biological research today is increasingly focusing on determining the positions within the cell of various cellular components to ever higher spatial resolutions. This involves many different techniques for enhancing resolution and contrast in images, both for electron microscopes (TEMs, STEMs, SEMs, etc.), as well as all types of light microscopes, including the latest super-resolution techniques. One powerful technique that has gained wide acceptance for research into cellular structure, transport, metabolism, and motility is the application of recombinant genetic techniques to link "reporter" genes to "genes of interest" (GoIs). Thus, when a particular GoI is expressed during normal genetic transcription/translation processes, the reporter gene will also be expressed, producing a small protein which ends up attached to the "protein of interest" (PoI) encoded for by the GoI. One widely-accepted reporter gene is that encoding for a green fluorescent protein (GFP), these reporter genes being available in wild and genetically-modified versions, and the expressed GFPs having fluorescence that extends from blue to yellow in emission wavelengths. The GFP is relatively small (29.6 kDa, 3 nm in diameter by 4 nm long) with its chromophore well protected inside and not requiring any co-factors for light emission. All that is needed to "light up" a GFP is illumination by a laser with a slightly shorter wavelength than the GFP emission wavelength. GFPs appear to be essentially "inert" to the proper functioning of their attached PoI—this is ensured in some cases by connecting the GFP to the PoI with a short flexible polypeptide "linker" which enables the GFP to swing around free from the protein, which may be part of some intracellular structure or mechanism that must not be interfered with in order to preserve the cellular functions being studied by the researcher.

Clearly, if the X-Y-Z location of the GFP can be determined precisely within a cell (say, to 10 nm accuracy) then the location of the PoI would be known to a similar accuracy. The fluorescing GFP can be observed through a light microscope and so the location of the PoI can be seen in the microscope relative to observable structures in the sample. Several techniques in the prior art have been proposed and, in some cases, demonstrated, for achieving high positional information from various fluorescent markers (FMs) such as GFPs and also quantum dots. In one technique, a green laser is used to excite a small portion of the fluorescent markers (FMs) in a sample, and the sample is then imaged. Using Gaussian curve fitting, the locations of the FMs may be determined within a FWHM of 20 nm, substantially smaller than the diffraction limit of the imaging system. Using multiple green laser flashes, alternating with red laser flashes which extinguish the fluorescence, the locations of a larger number of FMs may be determined in a process which may typically take tens of minutes. In another technique, described in U.S. Pat. No. 7,317,515 to Buijsse et al. for "Method of Localizing Fluorescent Markers," which is assigned to the assignee of the present application and which is hereby incorporated by reference, a charged particle beam scans the surface of the sample, damaging the markers and extinguishing the fluorescence when the beam hits the FM. The location of the FM corresponds to the position of the charged particle beam when the fluorescence is extinguished. Because the charged particle beam can be focused to a much smaller point than the laser that illuminates the marker, and the position of the charged particle beam at any time during its scan can be determined with great accuracy, the position of the FM, and therefore the position of the PoI, can be determined with similar accuracy.

Throughout all descriptions herein of the present invention, the term GFP will be used to represent the larger class of FMs which can be damaged by a charged particle beam (comprising electrons or ions), including GFPs, organic dyes, as well as inorganic markers such as quantum dots (which may typically be functionalized to enable selective attachment to particular intracellular components such as proteins, nucleic acids, etc.).

Many of the prior art methods for localization of FMs within biological samples work only for relatively small numbers of FMs, from which a small subset are activated at any one time—thus imaging times can be many minutes and still suffer from some of the limitations of light optical imaging. Prior art methods employing charged particle beams to selectively damage FMs within samples have utilized image processing methods capable of dealing only with relatively small numbers of FMs—for these methods, the statistical signal-to-noise ratio limits their application to FMs which do not inherently appear in large densities. For GFPs, in particular, this may be a hindrance, since any type of expressible tag (as opposed to a functionalized tag such as a quantum dot) can be created in very large numbers through normal cellular process of gene transcription to mRNA, followed by translation to proteins (GoI+linker+GFP). Thus, there is a need for a fast method for localization of very large numbers ($\geq 10000$) of FMs such as GFPs within cells, or sections of cells, in time frames, for example, of the order of a minute.

SUMMARY OF THE INVENTION

An object of the invention is to provide an improved method and apparatus for locating proteins of interest in a sample.

A preferred embodiment includes a charged particle apparatus and method capable of imaging samples containing fluorescent markers (FMs), such as green fluorescent proteins (GFPs) or quantum dots, using standard electron microscopic signals such as secondary electrons (SEs) or transmitted electrons (unscattered, elastically-scattered, and/or inelastically-scattered), while simultaneously exciting the FMs with a laser and collecting emitted light from the excited FMs.

One embodiment comprises a detector optics configuration which presents a very large collection solid angle for both secondary electrons and emitted light, without interference between the two types of detectors which would tend to reduce the respective collection solid angles for both SEs and light.

Some embodiments of the present invention comprise an exemplary image processing method potentially enabling larger (e.g., >10000) numbers of FMs to be simultaneously localized (during a single imaging scan of roughly a minute duration) than was possible with simpler image processing schemes in the prior art.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which:

FIG. 4A is a side view of both light and secondary electron trajectories for the detector optics in FIG. 3.

DETAILED DESCRIPTION OF PREFERRED EMBODIMENTS

Figure 2:
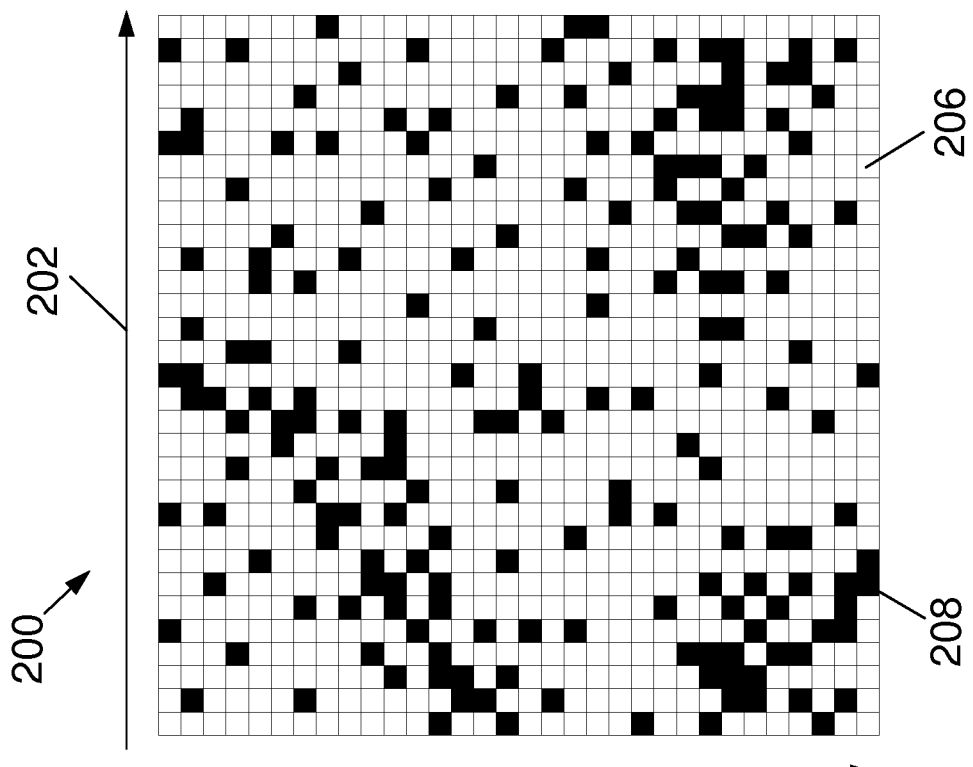
FIG. 2 is a schematic diagram of an X-Y scan raster, illustrating pixels containing GFPs and pixels without GFPs.

Some embodiments of the present invention provide charged particle systems comprising detector optics systems optimized for very high collection efficiencies for both secondary electrons and light simultaneously, without spatial interference between the two types of detectors. This is accomplished in some embodiments by at least one mirror, preferably a paraboloidal mirror, above and/or below the sample, such that the point on the sample surface impacted by the charged particle beam is at or in proximity to the focal point of the paraboloid(s) (either one or two). By the focal point being "in proximity to" the charged particle is meant that the area illuminated by the light reflected from the mirror includes, and is larger than, the area impacted by the charged particle beam.

In addition, a conducting surface, typically metallic, of the paraboloidal light mirror is electrically biased (typically a few hundred volts negative) to provide an electric field between the sample and the mirror to deflect secondary electrons so that they do not impact the mirror and to reflect the secondary electrons to a detector. Thus, both the photons and secondary electrons (SEs) emitted from the sample may be collected into large solid angles, preferably greater than $\pi/4$ steradians, more preferably greater than $\pi/2$ steradians, and even more preferably greater than $\pi$ steradians, providing efficiencies (and resultant higher signal-to-noise ratios) previously unattainable for detector systems in which the light and SE solid angles are spatially separated and mutually interfere. The secondary electron detector is preferably positioned below the point at which the charged particle beam exits mirror 314 in FIGS. 3, 4A and 4B.

In addition to these highly efficient light detection systems, issues of statistical (stochastic) noise in the light signal are addressed in some embodiments. This noise arises because the imaging mode of the present invention utilizes selective damage of single FMs such as GFPs due to the energetic charged particle (electron or ion) beam to localize each FM. Damaging a single FM results in an incremental loss in total light emission from the sample, e.g., if one FM out of a total of 10000 FMs is damaged, then the emitted light will decrease by roughly 0.01%. To detect such a small decrease in light emission, it is necessary that the stochastic noise due to fluctuations in light emission averaged over the pixel dwell time not be substantially larger than 0.01% in this example. Similar methods have been described in the prior art for smaller numbers of FMs, as in U.S. Pat. No. 7,317,515, assigned to the assignee of the present invention. In all these cases, the numbers of FMs which could be localized were limited.

The benefits of this improved signal-to-noise ratio in the light optical signal arising due to fluorescent emission from markers (such as GFPs, organic dyes, or quantum dots) in the sample are further amplified by another aspect of the present invention—an image processing method enabling the timing (and thus the locations) of FM damage events to be determined, even in the case of very large stochastic noise in the raw imaging signal.

Fluorescent Markers as Expressible Tags

Figure 1:
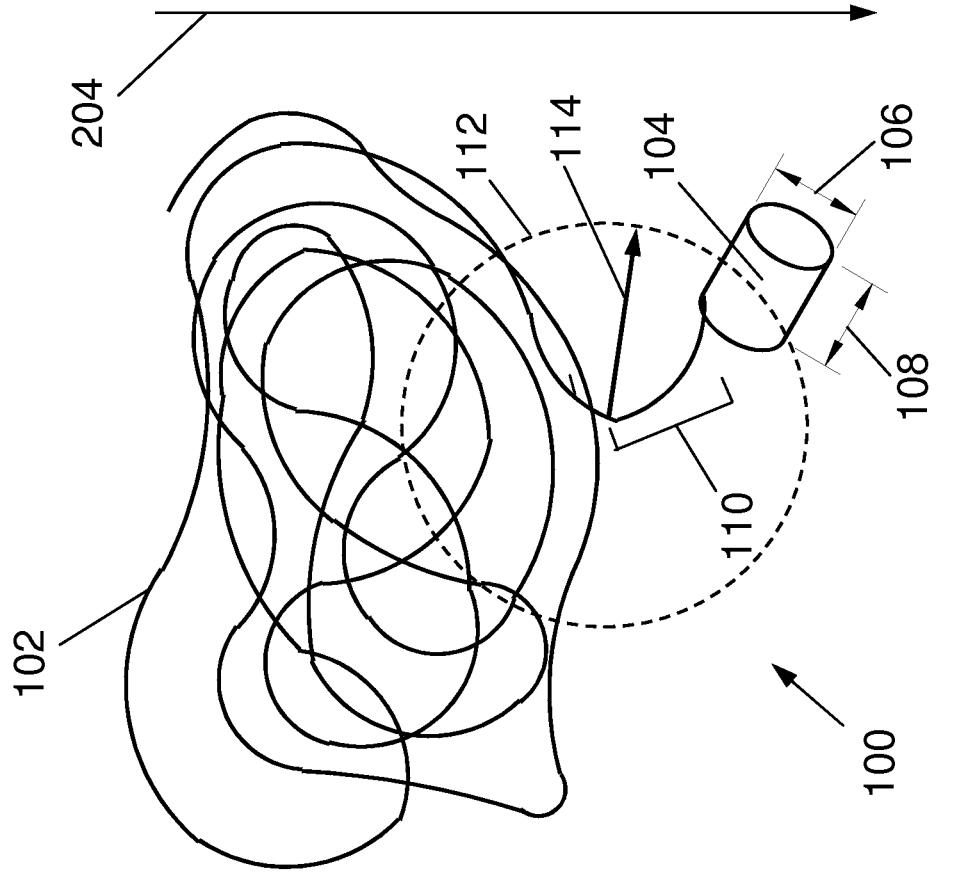
FIG. 1 shows a schematic diagram of a protein of interest (PoI), with a green fluorescent protein (GFP) attached by a linker.

FIG. 1 shows a schematic diagram 100 of a protein of interest (PoI) 102, with a green fluorescent protein (GFP) 104 attached by a linker peptide 110. A typical GFP has a diameter 106 of 3 nm and a length 108 of 4 nm—details of the "beta barrel" structure of the GFP 104 are omitted here. In general, the PoI 102 will be larger than the GFP 104, as shown. One key consideration in the use of expressible tags is that the tag does not interfere with the proper functioning of the PoI 102 within the cell, whether that function is metabolic, transport, structural, etc. Thus, a short peptide linker 110 is often used to attach the fairly rigid GFP 104 to the PoI 102, enabling the GFP 104 to swing around on an arc 112 of radius 114, as shown. Note that this radius 114 determines the maximum precision at which the GFP 104 can be located since GFP 104 is free to occupy any position on circle 112. Thus, it is likely that locating the GFP 104 to within 5 to 8 nm is sufficient for any position-determining methodology, as in the present invention, as well as in the prior art such as described in U.S. Pat. No. 7,317,515 assigned to the assignee of the present invention and incorporated herein by reference.

Methods for recombinantly-linking genes for reporter genes, such as for various versions of the "green fluorescent proteins" (GFPs) originating from the hydrozoan jellyfish species *Aequorea victoria* are well known. Since the original discovery of GFPs in the 1950s, a number of genetic variants have been developed with improved fluorescence spectra spanning an emission range from blue to yellow light, with simplified spectral absorption distributions. GFPs are relatively small cylinders ("beta barrels", 3 nm diameter by 4 nm long) comprising 238 amino acids (26.9 kDa), which appear to be essentially "inert" to the overall cellular mechanisms of species which can be far removed from jellyfish. Because of this, the use of GFPs is widely accepted in the biological community. What is particularly important is that the wide acceptance of GFPs as expressible markers makes the present invention potentially highly useful for the biological community in applications where current GFP localization methodologies are insufficiently precise. Throughout the descriptions of the operation of the three embodiments below, the GFPs should be understood to comprise a multiplicity of GFP variants, representing multiple recombinant reporter genes being expressed simultaneously in the biological samples being examined. Similarly, the light detectors in the three embodiments should be understood to comprise multiple detectors operating independently, and in parallel, each detecting light from a particular GFP type within the multiplicity of GFP types in the sample.

The present invention is applicable both to cases where a smaller number (10 to several 100) of GFPs are within the imaging field of view, as well as cases where there are many more (up to at least 10000) GFPs. The improved image processing method of the invention is applicable to both cases. Each GFP variant has its own unique spectral absorption and emission characteristics. An example is for the original "wild-type" GFPs (wtGFP) which has an absorption peak at 395 nm and an emission peak at 509 nm. Because the wtGFP has an undesirable second absorption peak at 475 nm, efforts were made to develop improved versions, such as the S65T mutation, having an absorption peak at 484 nm and an emission peak at 507 nm, with no secondary absorption peak. A key aspect in employing GFPs as expressible tags is that they may be present in very high numbers within the sample, necessitating the efficient light detection and image processing of the present invention.

Imaging Methodology for Fluorescent Markers in a Charged Particle System

FIG. 2 is a schematic diagram of a 32×32 X-Y scan raster 200, illustrating pixels containing GFPs 208 and pixels without GFPs 206. The fast scan axis 202 is along the X-direction, while the slow scan axis 204 is along the Y-direction. For normal raster scanning, the beam would first be positioned at the upper left and then moved to the upper right along the top row. Next, the beam would "retrace" back to the left side and move down one row, followed by scanning horizontally to the right again. This process is repeated until all 32×32=1024 pixels have been imaged. In the example here, white pixels 206 represent those not containing a GFP, while black pixels 208 contain a single GFP. It is assumed that the GFP density is low enough that Poisson statistics apply and we can make the approximation that no pixels contain more than one GFP. Since the GFPs are expressible tags representing the locations within a cell (or slice of a cell) of a particular Protein of Interest (PoI), the distribution of GFPs will often be non-uniform, representing the non-uniform distribution of PoIs due to their required locations within the cell for proper functioning.

Three exemplary system configurations are presented below: a first configuration which is applicable to thick samples and collects all signals from the front surface of the sample (i.e., operating in SEM mode); a second configuration with the detector optics for electrons and light below the sample (i.e., operating in a TEM or STEM mode); and a third configuration with a combined detector system both above and below the sample to give the maximum possible collection efficiency for light emitted from excited FMs within the sample.

First Embodiment

Detector Optics Above the Sample

Figure 3:
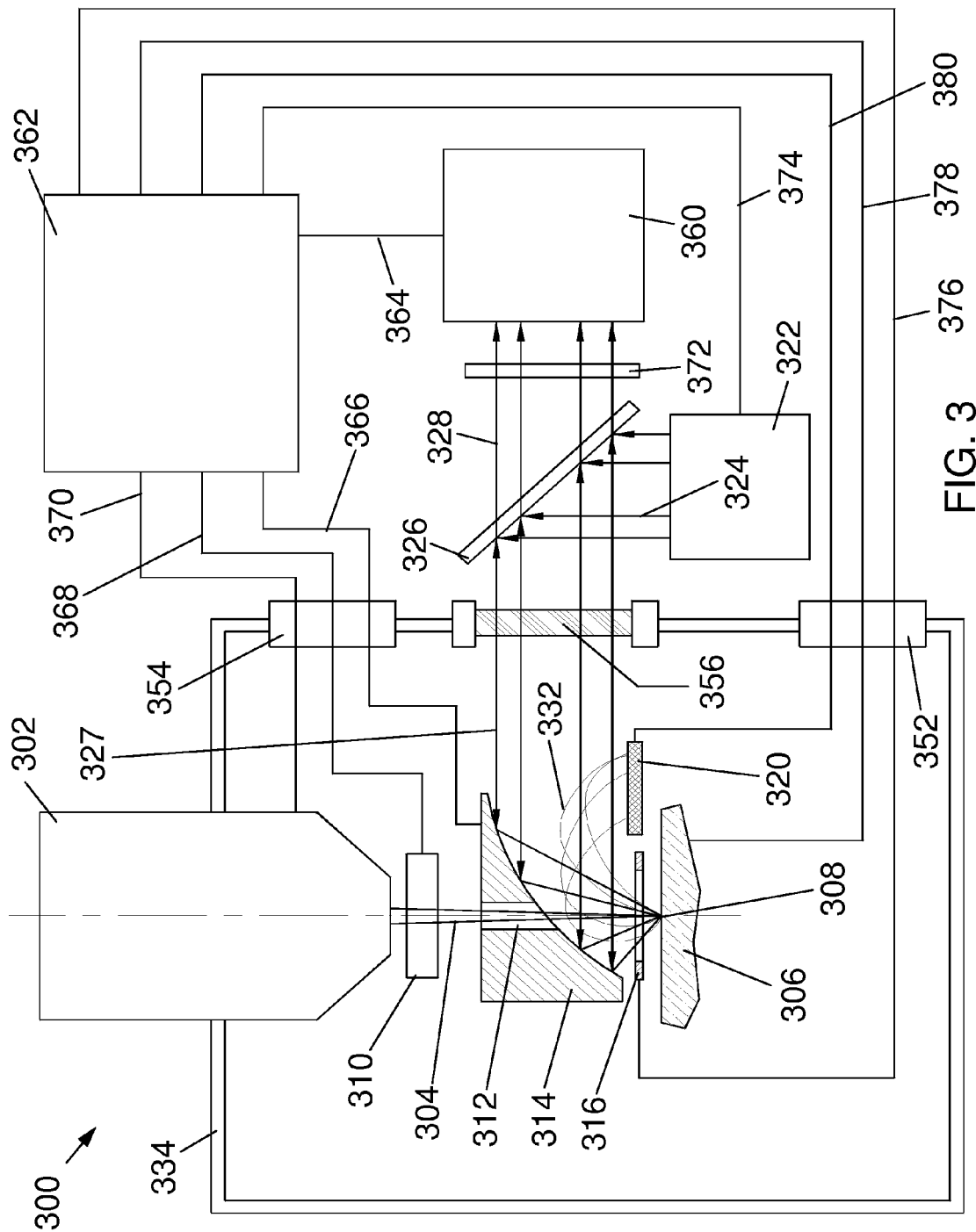
FIG. 3 is a schematic diagram of a first embodiment of the present invention comprising detector optics above the sample.

FIG. 3 is a schematic diagram of a first embodiment 300 of the present invention comprising detector optics above the sample 306. Sample 306 may include a biological sample including fluorescent markers that are expressed by genes linked to genes of interest or including inorganic markers that selectively attach to particular intracellular components. Sample 306 may also include a biological sample including dyes or other inorganic markers, such as quantum dots, that are functionalized to enable selective attachment to particular intracellular components. Sample 306 sits on a sample stage at a sample position that defines a sample plane.

A charged particle column 302, such as an electron beam column or a focused ion beam column, generates a beam 304 of charged particles that is focused by column 302 onto the surface of a sample 306 at a location 308. Electrons in the beam typically have energies of between 1,000 eV and 25,000 eV. Ions typically have energies of between 5,000 eV and 50,000 eV. An X-Y beam deflector 310, which may comprise magnetic coils, electrostatic multipoles, or a combination of both magnetic coils and electrostatic multipoles, is configured to move the beam 304 around on the surface of the sample 306, typically in an X-Y raster pattern for imaging, as in FIG. 2.

In this first embodiment 300 of the invention, the sample 306 is assumed to be thick enough to prevent penetration of the beam 304 through the sample 306, thus all imaging signals (both light and charged particles) are collected above the sample surface as shown. A paraboloidal mirror 314 is positioned between the deflector 310 and the sample 306. A hole 312 in mirror 314 allows passage of beam 304 downwards to the sample 306. Below the mirror 314 is a flat shield plate 316, typically biased to the same voltage as the sample 306. In order to achieve maximum collection efficiency for light, mirror 314 is configured to subtend the largest possible solid angle, preferably greater than $\pi$ steradians, at location 308. Then the maximum possible amount of light emitted from the fluorescent markers (FMs) at location 308 will be collected and transmitted through the beam splitter 326, then through color filter 372, and finally to detector 360—this maximizes the achievable signal-to-noise ratio in the optical signal.

The fluorescent markers (FMs) are excited by light 324 from laser 322, which is emitted upwards, reflected first off beam splitter 326 and then reflected and focused by the paraboloidal mirror 314 onto the surface of sample 306 at location 308. Note that it is desirable to have the largest possible transmission of emitted light from the FMs through beam splitter 326 in order to increase the amount of light reaching detector 360. If the transmission of beam splitter 326 is 50%, then half the signal light 327 from location 308 will get to the detector 360, and half of the excitation light 324 from laser 322 will reach location 308. Thus, to focus 3 mW from laser 322 onto location 308 would require a 6 mW laser output 324 (ignoring other reflective losses). If ample laser power is available, it may be preferred to increase the transmission (and thus reduce the reflectivity) of beam splitter 326, for example to 80%. Then 80% of the light from location 308 (again, ignoring reflective losses) will pass through the beam splitter 326, while only 20% of the light 324 from laser 322 will reach location 308—thus, to focus 3 mW at location 308, a 15 mW laser output power 324 would be required (12 mW would pass through beam splitter 326, to be absorbed in a beam dump (not shown) above splitter 326). In this embodiment, the light from laser 322 is reflected by mirror 314 onto the top surface of sample 306, that is, the light does not first pass through sample 306 before being reflected by mirror 314 and the light from the source illuminates the sample initially from above the sample. Similarly, light emitted by fluorescent markers within sample 306 are emitted through the top surface of sample 306, collected by mirror 314 above sample 306, and reflected to light detector 360 without passing completely through sample 306 and being collected on the opposite side of the mirror, as in U.S. Pat. No. 7,317,515.

The second function of paraboloidal mirror 314 is to provide a conductor that can be electrically biased to provide an electric field that prevents secondary electrons from impacting mirror 314 by reflecting secondary electrons (SEs) 332 emitted from location 308 due to the impact of the primary charged particle beam 304. This is shown in more detail in FIGS. 4A and 4B. SEs 332 are deflected by a several hundred volt negative potential applied to the (conducting) mirror surface. Note that the SEs do not reflect the same way that the light 328 does, because the SEs are reflected by the electrostatic field created by the voltage applied to the mirror 314 or other conductor, and this field extends throughout the entire volume of the paraboloidal mirror 314 (see FIG. 4B for an isometric view of mirror 314). The SEs 332 are deflected toward a detector 320 and collected by the detector 320 as shown to the side of the sample 306. Thus, both the light and secondary electrons are collected from location 308 with high efficiencies since there is no conflict between the collection solid angles for light and SEs. The size of hole 312 is preferably kept to a minimum to reduce both loss in light reflection and any perturbations to the electrostatic field deflecting the secondary electrons. The focal point of the paraboloidal mirror 314 is approximately at location 308 on the surface of sample 306—thus light emitted from the vicinity of location 308 will be focused into roughly parallel light beams 328, directed towards the right of FIG. 3. While it is preferred that the electric field that directs the SEs away from the mirror be produced by the conductive mirror, the electric field can be produced by a conductor that is separate from the mirror. An electrical bias can also be applied to the entrance of the charged particle detector 320.

A system controller 362 is electrically connected to column 302 through cable 370, to X-Y deflector 310 through cable 368, to mirror 314 through cable 366, to shield plate 316 through cable 376, to sample 306 through cable 378, to SE detector 320 through cable 380, and to laser 322 through cable 374. The system controller 362 coordinates the scanning of beam 304 by the X-Y deflector 310 with the display of an image on a monitor (not shown), as well as performing the image processing calculations described below to locate FMs on the sample surface.

Charged particle beams typically must travel in a vacuum, thus a vacuum enclosure 334 contains the exit of column 302, X-Y deflector 310, mirror 314, shield plate 316, and sample 306, as shown. Typically, it is much easier to locate as much of the light optical instrumentation outside the vacuum as possible, thus a viewport 356 allows the light 327 from laser 322 (reflected off beam splitter 326) to pass into enclosure 334, while the light emitted from FMs at location 308 is allowed to pass out from enclosure 334, through beam splitter 326, then through color filter 372 and into detector 360. Color filter 372 serves to reduce the amount of laser excitation light 324 which can pass into detector 360. Since the excitation light always has a shorter wavelength than the emitted light from the FMs, it is possible to tune the passband of filter 372 to transmit most of the light from the FMs, while blocking most of the laser light. In some cases, additional light filtering may take place within detector 360. Electrical feedthrough 354 allows the passage of cables 366, 368 and 370 into and out of enclosure 334, while feedthrough 352 allows the passage of cables 376, 378 and 380 into and out of enclosure 334.

Detector Optics for High Efficiency Collection of Light and Secondary Electrons

FIG. 4A is a side cross-sectional view 400 generated using the SIMION ray-tracing program showing both light and secondary electron trajectories for the detector optics in FIG. 3. The primary beam 304 can be seen passing downwards through hole 312 in the paraboloidal mirror 314. Impact of beam 304 with sample 306 at location 308 induces the emission of secondary electrons 332 into a cosine (Lambert Law) distribution. Shield plate 316 and sample 306 generally have the same voltage applied by system controller 362 (see FIG. 3). Several hundred volts negative bias is applied to the conductive mirror surface 314 to repel the (0 to 50 eV) secondary electrons 332 as shown. This reflection differs from that of the light reflecting specularly off mirror 314, thus the SEs are collected on detector 320 to the side of sample 306. The collection solid angle at location 308 is very high, preferably greater than $\pi$ steradians, in this configuration, giving a good signal-to-noise SE image. Light emitted from the fluorescent markers (FMs) in the sample 306 is also emitted into a cosine distribution, a large fraction of which is directed towards mirror 314, as shown. Since location 308 on sample 306 is the focal point of paraboloidal mirror 314, light 328 reflecting off mirror 314 is generally parallel passing to the right of the FIG. 4A. It will be understood that the benefits of the mirror 314 can be used in other applications in which light is directed toward a sample or detected from a sample in a charged particle beam system. Such systems that would benefit from mirror 314 include systems that collect light for an optical microscope that is coaxial with a charged particle beam, such as the system described in U.S. Pat. No. 6,373,070 to Rasmussen for "Method apparatus for a coaxial optical microscope with focused ion beam," and systems that collect light from photo luminescence caused by the charged particle beam, or luminescence.

Figure 4B:
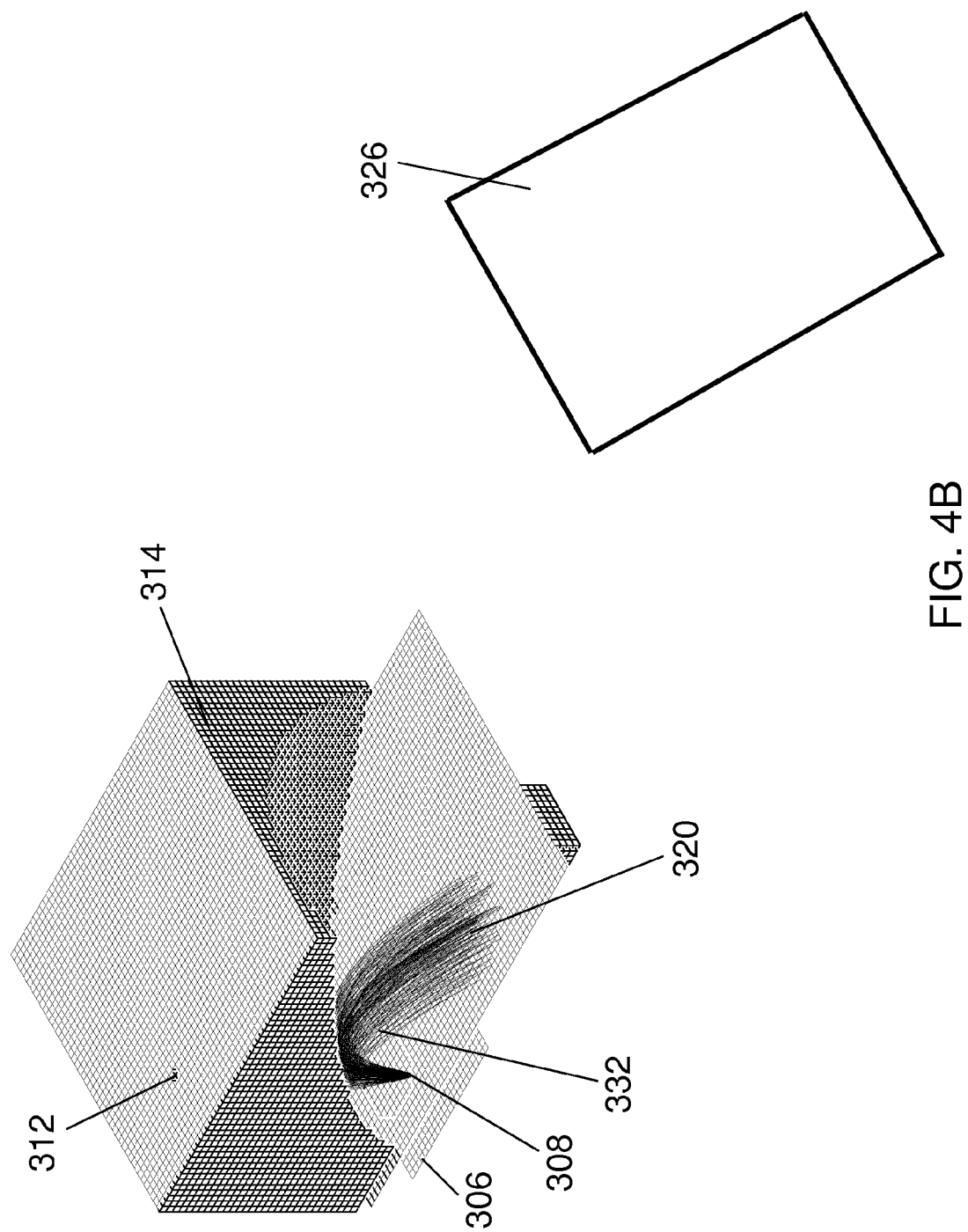
FIG. 4B is a cutaway isometric view of the detector optics in FIGS. 3 and 4A.

FIG. 4B is a cutaway isometric view of the detector optics in FIG. 4A, also generated using SIMION. In addition, the beam splitter 326 is shown at the lower right. The elliptical pattern of SE 332 impacts at detector 320 can be seen, thus the area of detector 320 need not be excessively large—smaller detector areas may increase the detector bandwidth (at least for solid-state detectors) and thus are generally preferred.

Second Embodiment

Detector Optics Below the Sample

Figure 5:
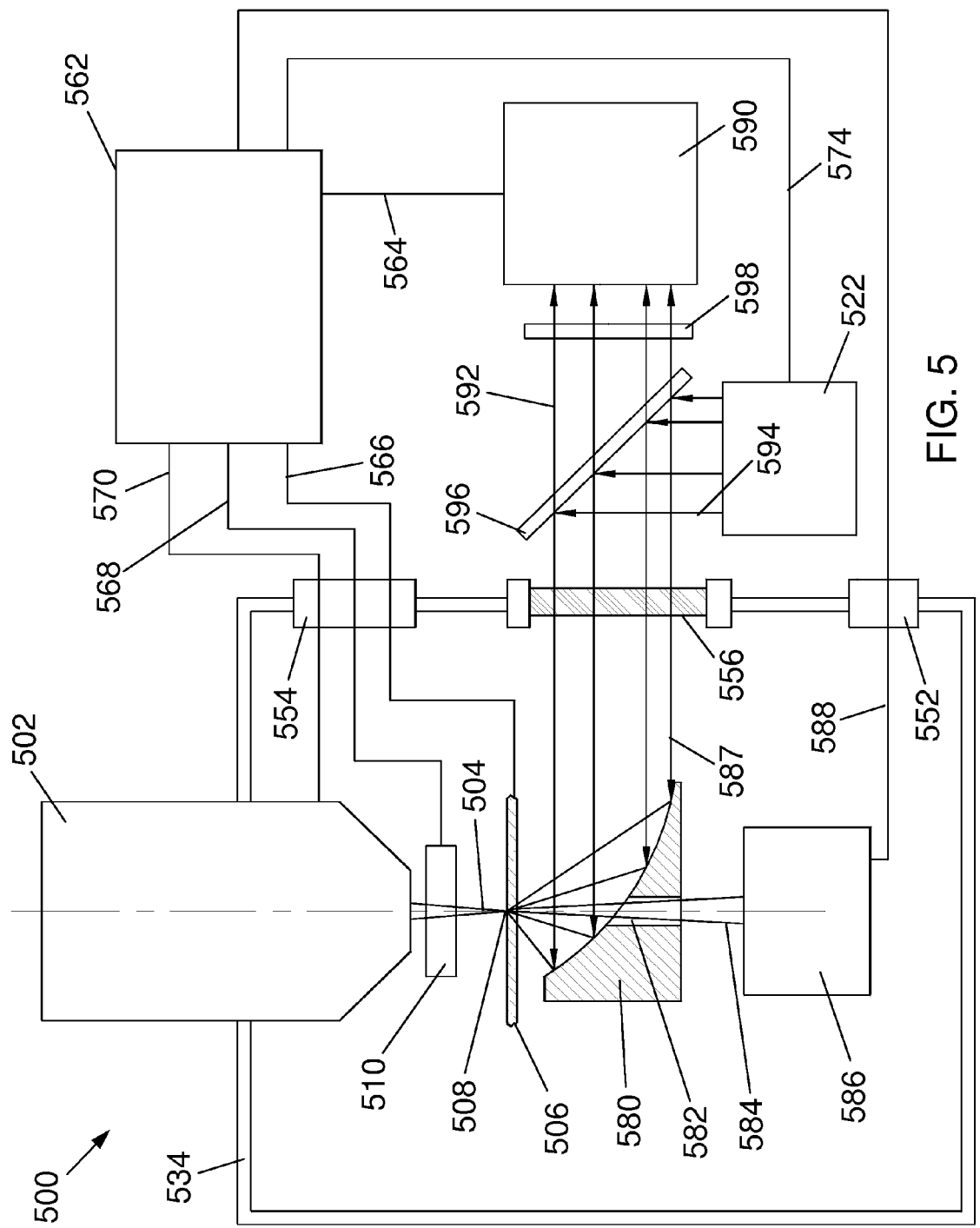
FIG. 5 is a schematic diagram of a second embodiment of the present invention comprising detector optics below the sample.

FIG. 5 is a schematic diagram of a second embodiment 500 of the present invention comprising detector optics below a sample 506. A charged particle column 502, such as an electron beam column or a focused ion beam column, generates a beam 504 of charged particles which is focused by column 502 onto the surface of the sample 506 at a location 508. Beam 504 typically includes electrons having energies between about 50 keV and 300 keV. An X-Y beam deflector 510, which may comprise magnetic coils, electrostatic multipoles, or a combination of both magnetic coils and electrostatic multipoles, is configured to move the beam 504 around on the surface of the sample 506, typically in an X-Y raster pattern for imaging. In this second embodiment 500 of the invention, the sample 506 is assumed to be thin enough to permit penetration of the beam 504 through the sample 506, thus all imaging signals (both light and charged particles) are collected below the sample surface as shown. A paraboloidal mirror 580 is positioned below the sample 506. A hole 582 in mirror 580 allows the travel of transmitted charged particle beam 584 downwards after passage through sample 506. Beam 584 may typically comprise unscattered particles from the primary beam 504, elastically-scattered particles, inelastically-scattered particles, secondary electrons and/or ions, and particles which have scattered both elastically and inelastically in the sample 506. After passing through hole 582, beam 584 enters detector 586 which may comprise energy filters to differentiate between transmitted particles of the various types cited above, and possibly multiple detectors operating in parallel.

In order to achieve maximum collection efficiency for light, mirror 580 is configured to subtend the largest possible solid angle (typically >π steradians) at location 508. Thus, the maximum possible amount of light emitted from the fluorescent markers (FMs) at location 508 will be collected and transmitted through beam splitter 596, then through color filter 598, and finally to light detector 590—this maximizes the achievable signal-to-noise ratio in the optical signal. The FMs are excited by light 594 from laser 522, which is emitted upwards, reflected first off beam splitter 596 and then reflected and focused by paraboloidal mirror 580 through sample 506 at location 508. Note that it is desirable to have the largest possible transmission of light through beam splitter 596 in order to increase the amount of light reaching detector 590—the same percentage transmission considerations apply here as for FIG. 3, above. It is important that the size of hole 582 be kept to a minimum to reduce loss in light reflection, while remaining large enough to accommodate the elastically-scattered electrons within beam 584. The focal point of the paraboloid 580 is at approximately location 508 on sample 506—thus light emitted from the vicinity of location 508 will be focused into roughly parallel light beams 587, directed towards the right of the figure.

A system controller 562 is electrically connected to column 502 through cable 570, to X-Y deflector 510 through cable 568, to sample 506 through cable 566, to laser 522 through cable 574, to detector 590 through cable 564, and to detector 586 through cable 588. System controller 562 coordinates the scanning of beam 504 by X-Y deflector 510 with the display of an image on a monitor (not shown), as well as performing the image processing calculations described below to locate FMs on the sample surface.

Charged particle beams typically must travel in a vacuum, thus a vacuum enclosure 534 contains the exit of column 502, X-Y deflector 510, sample 506, mirror 580, and detector 586, as shown. Viewport 556 allows the light 587 from laser 522 (reflected off beam splitter 596) to pass into enclosure 534, while the light emitted from FMs at location 508 is allowed to pass out of enclosure 534, through beam splitter 596, then through color filter 598, and into detector 590. Color filter 598 serves to reduce the amount of laser excitation light 594 which can pass into detector 590, as for the first embodiment in FIG. 3. The same reflectivity considerations apply here for beam splitter 596 as for beam splitter 326 in FIG. 3. Electrical feedthrough 554 allows the passage of cables 566, 568 and 570 into and out of enclosure 534, while feedthrough 552 allows the passage of cable 588 into and out of enclosure 534.

Third Embodiment

Detector Optics Both Above and Below the Sample

Figure 6:
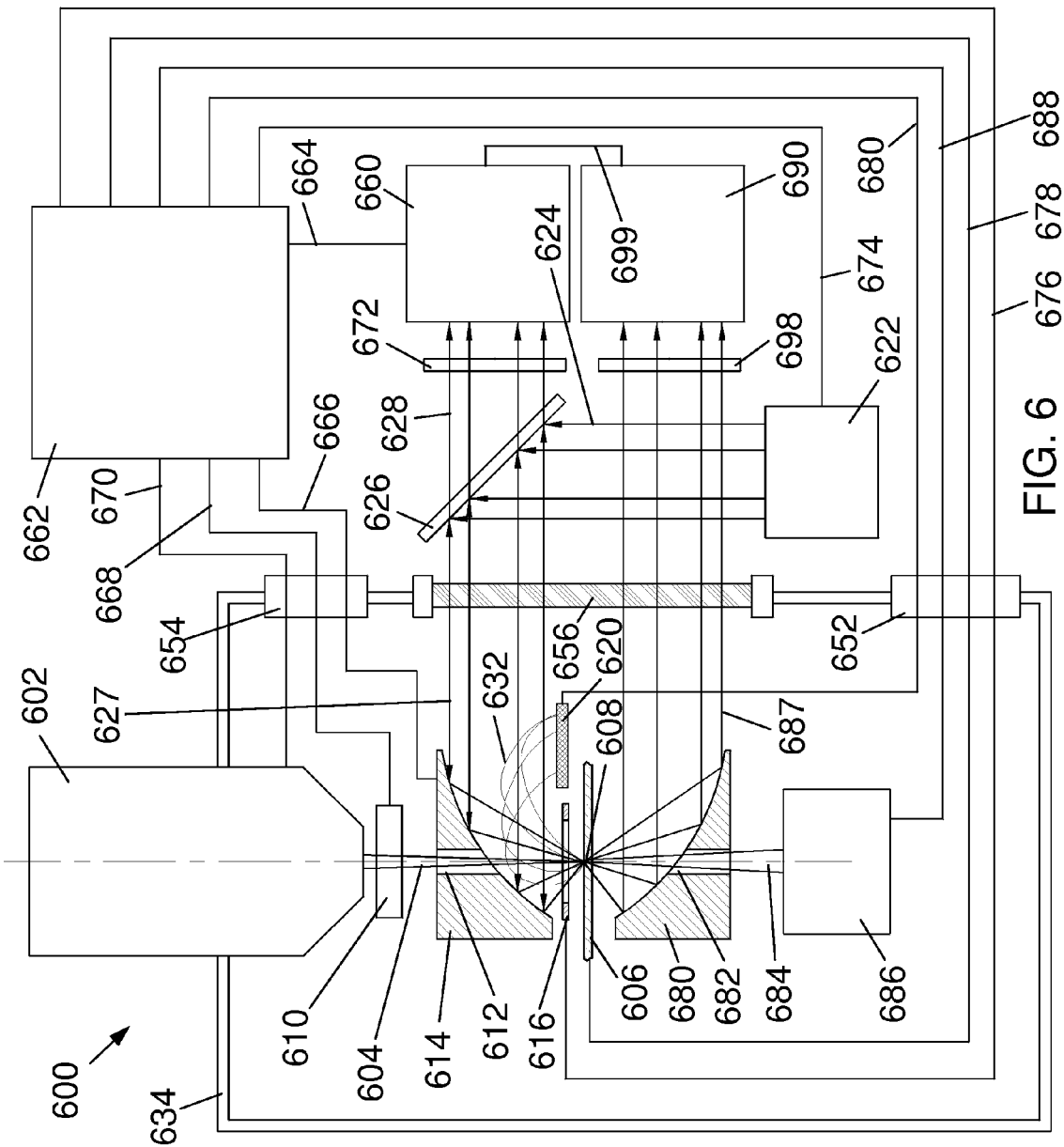
FIG. 6 is a schematic diagram of a third embodiment of the present invention comprising detector optics both above and below the sample.

FIG. 6 is a schematic diagram of a third embodiment 600 of the present invention comprising detector optics both above and below the sample 606. A charged particle column 602, such as an electron beam column or a focused ion beam column, generates a beam 604 of charged particles which is focused by column 602 onto the surface of a sample 606 at a location 608. An X-Y beam deflector 610, which may comprise magnetic coils, electrostatic multipoles, or a combination of both magnetic coils and electrostatic multipoles, is configured to move the beam 604 around on the surface of the sample 606, typically in an X-Y raster pattern for imaging. In this third embodiment 600 of the invention, the sample 606 is assumed to be thin enough to permit penetration of the beam 604 through the sample 606. To achieve larger collection efficiencies for light, two paraboloidal mirrors 614 and 680 are positioned above and below the sample 606, respectively. A hole 612 in mirror 614 allows passage of beam 604 to the sample 606. A hole 682 in mirror 680 allows passage of transmitted charged particle beam 684 downwards after passage through sample 606. Beam 684 may typically comprise unscattered particles from primary beam 604, elastically-scattered particles, inelastically-scattered particles, secondary electrons and/or ions, and particles which have scattered both elastically and inelastically in sample 606. After passing through hole 682, beam 684 enters detector 686 which may comprise energy filters to differentiate between transmitted particles of the various types cited above, and possibly multiple detectors operating in parallel. The considerations for collection of SEs 632 emitted from location 608 due to the impact of primary beam 604 into detector 620 are the same as in FIGS. 3, 4A and 4B.

In order to achieve maximum collection efficiency for light, both mirrors 614 and 680 are configured to subtend the largest possible solid angles (typically >π steradians for each of mirrors 614 and 680, giving a total >2π steradians) at location 608. The maximum possible amount of upwards-emitted light emitted from the fluorescent markers (FMs) at location 608 will be collected and transmitted through the beam splitter 626, then through color filter 672, and into detector 660—this maximizes the achievable signal-to-noise ratio in the optical signal. Similarly, the maximum possible amount of downwards-emitted light from the FMs at location 608 will be collected and transmitted through color filter 698 and then to detector 690. The FMs are excited by light 624 from laser 622, which is emitted upwards, reflected first off beam splitter 626 and then reflected and focused by paraboloidal mirror 614 onto sample 606 at location 608. Note that it is desirable to have the largest possible transmission of light through beam splitter 626 in order to increase the amount of light reaching detector 660—the same percentage transmission considerations apply here as for FIGS. 3 and 5, above. It is important that the size of holes 612 and 682 be kept to a minimum to reduce loss in light reflection. The focal points of paraboloids 614 and 680 are at approximately location 608 on sample 606—thus light emitted from the vicinity of location 608 will be focused into roughly parallel light beams 628 and 687, respectively, directed towards the right of the figure.

A system controller 662 is electrically connected to column 602 through cable 670, to X-Y deflector 610 through cable 668, to mirror 614 through cable 666, to detectors 660 and 690 through cable 664, to shield plate 616 through cable 676, to sample 606 through cable 678, to detector 686 through cable 688, and to laser 622 through cable 674. Detectors 690 and 660 are shown interconnected through cable 699, however, an alternative configuration would have separate cables to system controller 662. System controller 662 coordinates the scanning of beam 604 by the X-Y deflector 610 with the display of an image on a monitor (not shown), as well as performing the image processing calculations described below to locate FMs on the sample surface.

Charged particle beams typically must travel in a vacuum, thus a vacuum enclosure 634 contains the exit of column 602, X-Y deflector 610, mirror 614, shield plate 616, sample 506, mirror 680, and detector 686, as shown. It is much easier to locate as much of the light optical instrumentation outside the vacuum as possible, thus a viewport 656 allows the light 624 from laser 622 (reflected off beam splitter 626) to pass into enclosure 634, while the upwards-emitted light from FMs at location 608 is allowed to pass out of enclosure 634, through beam splitter 626, then through color filter 672 and into detector 660. The downwards-emitted light from FMs at location 608 passes out of enclosure 634 through viewport 656, through color filter 698, and then into detector 690. Color filters 672 and 698 serve to reduce the amount of laser excitation light 624 which can pass into detectors 660 and 690, respectively, as for the first embodiment in FIGS. 3 and 5. Electrical feedthrough 654 allows the passage of cables 666, 668 and 670 into and out of enclosure 334, while feedthrough 652 allows the passage of cables 676, 678, 688, and 680 into and out of enclosure 634. Note that in this dual paraboloidal mirror configuration, light from laser 622 which passes through sample 606 unabsorbed will reflect off mirror 680 towards detector 690—thus color filter 698 must be configured to withstand a potentially high level of laser illumination, higher than would be the case in FIGS. 3 and 5.

Imaging of Smaller Numbers of Fluorescent Markers in the Scan Field

Figure 7:
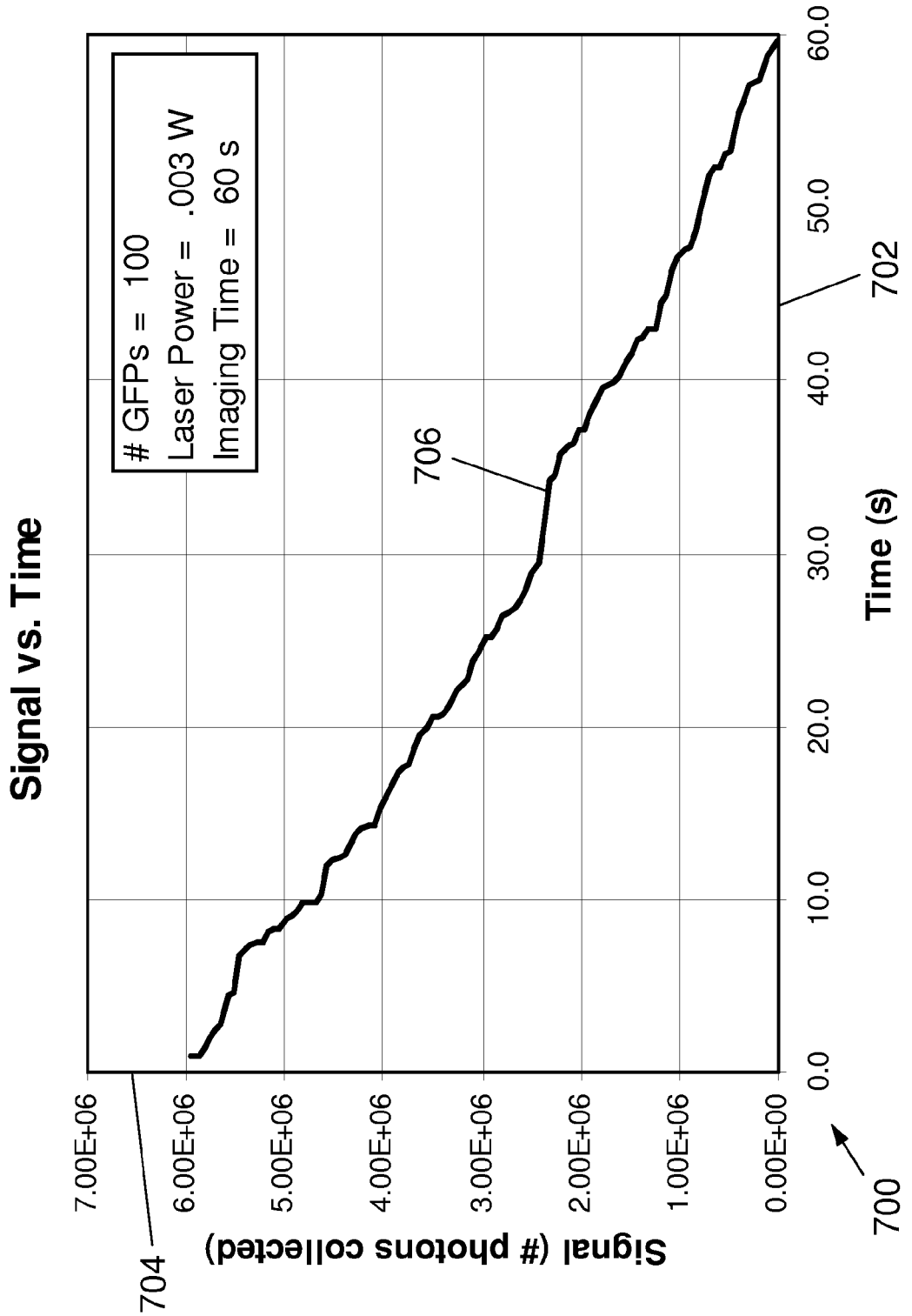
FIG. 7 is a graph of the signal as a function of the time during a raster scan for a scan field containing 100 GFPs.

FIG. 7 is a graph 700 of the signal 704 (number of photons collected per pixel) as a function of the time 702 during a raster scan for a scan field containing 100 GFPs. The overall scan time is 60 s, distributed over 512×512 (256 k) pixels, with a pixel dwell time of 229 μs. Curve 706 represents the number of photons collected per pixel for all the undamaged GFPs within the illuminated area. At the far left, all 100 GFPs are assumed to be emitting light in response to laser excitation. As curve 706 descends towards the lower right, the number of damaged GFPs is gradually increasing from 0 to 100, with eventually all GFPs damaged at the end of the 60 s raster. Because the GFPs are randomly located, curve 706 has some irregularities while following an overall descent from 0 s to 60 s. The laser power of 3 mW is distributed over a 28 μm² area at the sample—in this example, the raster is assumed to have this same area, thus at the end of the scan, no GFPs remain undamaged. In general, the illuminated area may be larger than the raster, thus some GFPs would remain undamaged at the end of the scan at 60 s.

Figure 8:
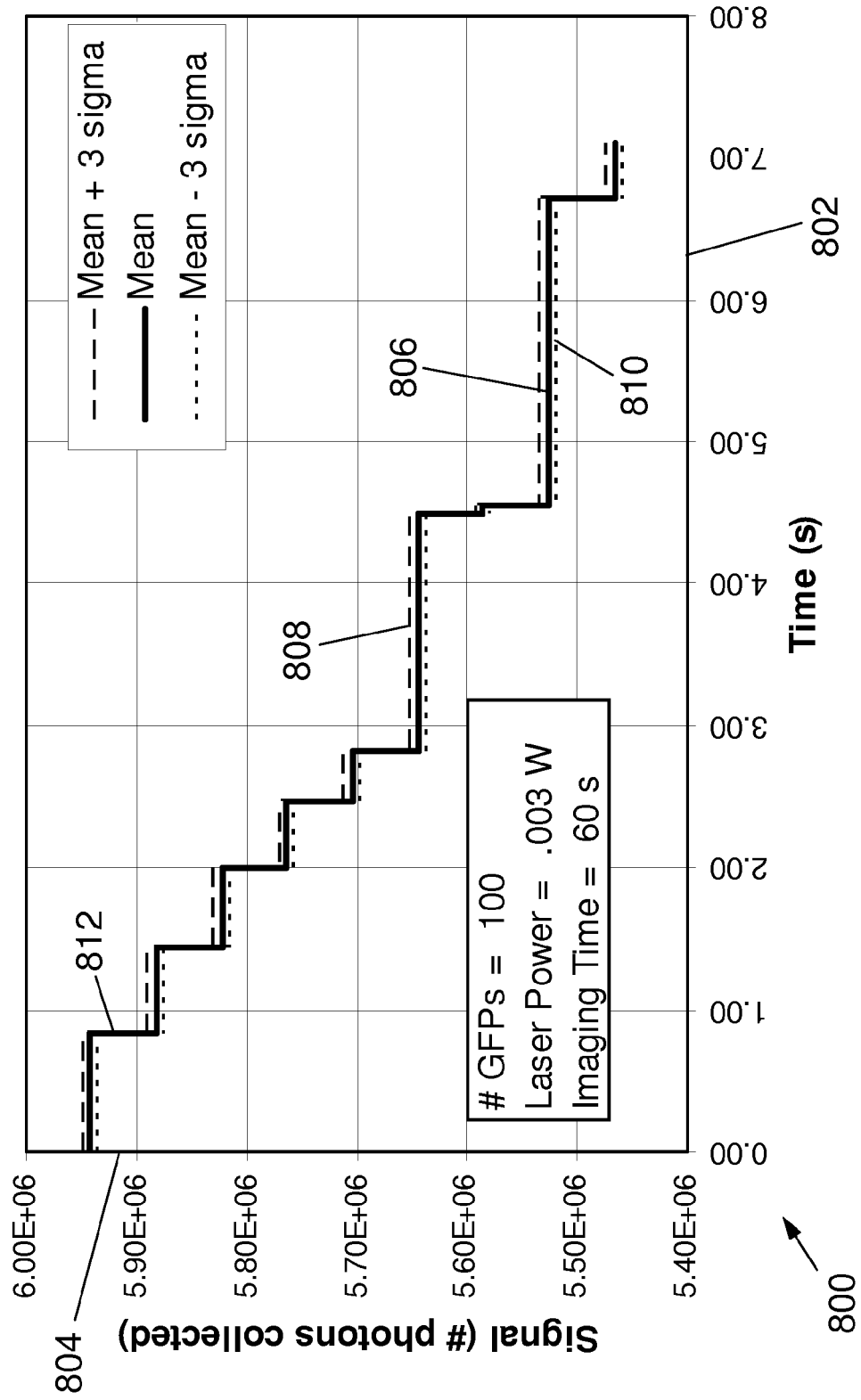
FIG. 8 is a graph showing a close-up of the beginning of the graph in FIG. 7, showing damage to the first eight GFPs out of the total of 100.

FIG. 8 is a graph 800 showing a close-up of the beginning of the graph 700 in FIG. 7, showing damage to the first eight GFPs out of the total of 100. The most difficult point in the localization of the GFPs within the area illuminated by the laser is at the beginning when there is the maximum number of GFPs emitting (and the minimum number of GFPs already damaged). This is because with the largest number of undamaged GFPs emitting light, the statistical fluctuations in the total collected light from all GFPs will be the largest (calculated as the square root of the number of photons collected in the pixel dwell time). Graphs 700 and 800 were made with the assumptions listed in Table I. Curve 806 represents the mean number of photons collected from all the undamaged GFPs in the illuminated area as a function of time into the scan—only the first 8 s are shown, during which time eight GFPs are struck and damaged by the charged particle beam (electrons or ions). Each of these damage events is represented by a vertical drop in the signal, such as drop 812 at the upper left. Above curve 806 is the +3σ curve 808 (long dashes), representing expected signal fluctuations three standard deviations above the mean signal level 806—a relatively unlikely event. Similarly, below curve 806 is the −3σ curve 810 (short dashes), representing expected signal fluctuations three standard deviations below the mean signal level 806—also a relatively unlikely event. The key thing to note here is that at jump 812, representing the loss (due to damage) of one GFP, curve 810 at the left of jump 812 is well above curve 808 at the right of jump 812—in other words, it is extremely unlikely that the inherent statistical signal-to-noise arising from the number of photons collected from all the undamaged GFPs will make it difficult to detect a single GFP damage event, in the case where there are only 100 GFPs being illuminated (and thus emitting) within the laser focused area.

TABLE I

Assumptions for Graphs 700 and 800 in FIGS. 7 and 8.

| | |
|---|---|
| Total Imaging time | 60.00 s |
| Image dimension | 512 # pixels/side |
| Total # pixels | 262144 |
| Pixel time | 228.9 us |
| Laser power at substrate | 0.0030 W = J/s |
| Wavelength | 550.00 nm |
| Energy/photon | 2.25 eV = (in J) |

TABLE I-continued

Assumptions for Graphs 700 and 800 in FIGS. 7 and 8.

| | |
|---|---|
| Incident photons/s | 8.306E+15 /s |
| Diameter of illuminated area | 6.00 um |
| Area of illuminated area | 28.27 um^2 |
| Diameter of GFP | 3.00 nm |
| Area of GFP | 7.07 nm^2 |
| Incident photons/s/GFP | 2.077E+09 /s |
| quantum efficiency estimate | 0.50 |
| collection efficiency estimate | 0.25 |
| photons collected/s/GFP | 2.596E+08 /s/GFP |
| photons collected/pixel/GFP | 59410.21 |
| statistical fluctuation in #photons/pixel/GFP | 243.74 |
| Number of GFP in illuminated area | 100 |
| photons collected/pixel time/illum. area | 5.941E+06 |
| statistical fluctuation in #photons/illum. area | 2437.42 |
| Signal/Noise estimate | 24.37 |

Imaging of Larger Numbers of Fluorescent Markers in the Scan Field

Figure 9:
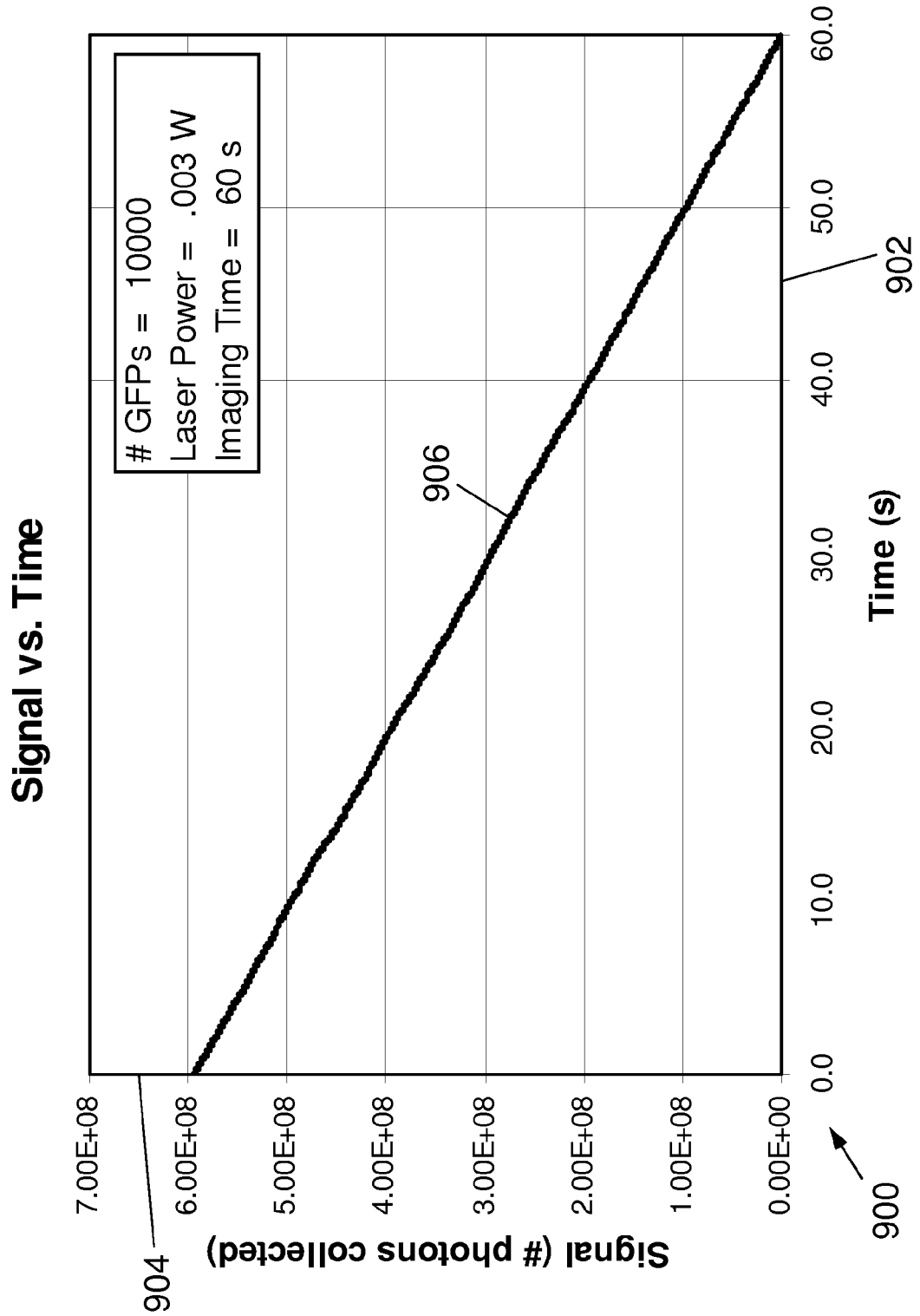
FIG. 9 is a graph of the signal as a function of the time during a raster scan for a scan field containing 10000 GFPs.

FIG. 9 is a graph 900 of the signal 904 (number of photons collected per pixel) as a function of the time 902 during a raster scan for a scan field containing 10000 GFPs. The overall scan time is 60 s, distributed over 512×512 (256 k) pixels, with a pixel dwell time of 229 μs, as in FIG. 7. Curve 906 represents the number of photons collected per pixel for all the undamaged GFPs within the illuminated area. At the far left, all 10000 GFPs are assumed to be emitting light in response to laser excitation. As curve 906 descends almost linearly towards the lower right, the number of damaged GFPs is gradually increasing from 0 to 10000, with eventually all GFPs damaged at the end of the 60 s raster. Because 10000 is such a large number, even though the GFPs were randomly distributed in the field of view, curve 906 is approximately a straight line. The laser power of 3 mW is distributed over a 28 μm² area at the sample—in this example, the raster is assumed to have this same area, thus at the end of the scan, no GFPs remain undamaged. In general, the illuminated area may be larger than the scan raster, thus some GFPs would remain undamaged at the end of the raster.

Figure 10:
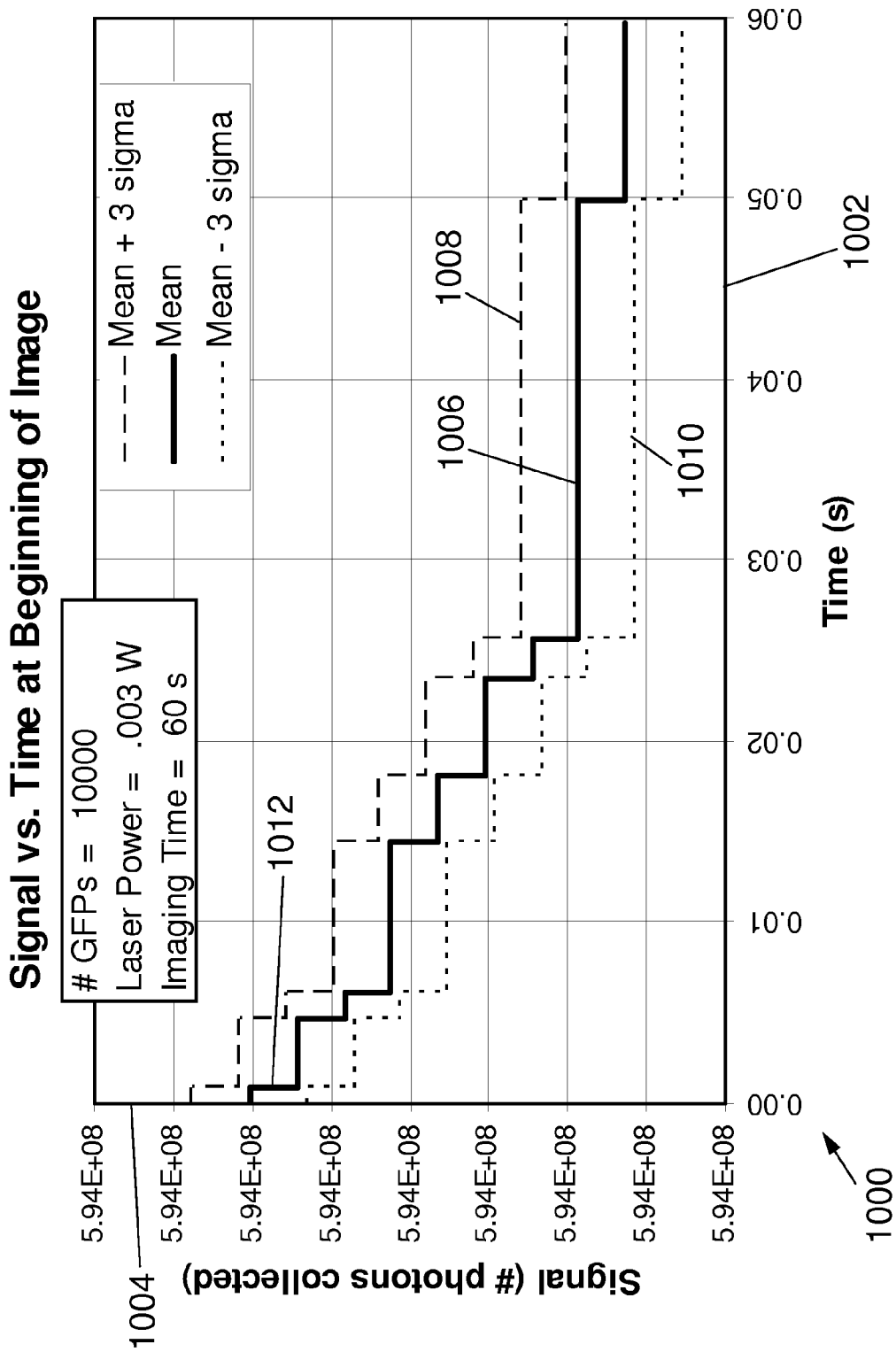
FIG. 10 is a graph showing a close-up of the beginning of the graph in FIG. 9, showing damage to the first eight GFPs out of the total of 10000.

FIG. 10 is a graph 1000 showing a close-up of the beginning of the graph 900 in FIG. 9, showing damage to the first eight GFPs out of the total of 10000. As was the case for graph 700 in FIG. 7, the most difficult point in the localization of the GFPs within the area illuminated by the laser is at the beginning when there is the maximum number of GFPs emitting (and the minimum number of GFPs already damaged). Graphs 900 and 1000 represent a hundred times more GFPs in the area illuminated by the laser than was the case in FIGS. 7 and 8—thus the total light collected (see the three alternative detector geometries in FIGS. 3, 5, and 6) will be a hundred times higher, with √100=10 times higher absolute statistical fluctuations. Since the light emitted by a single GFP is independent of the total number of illuminated GFPs, this means that the change in total light collected (from all the undamaged GFPs) whenever a single GFP is damaged by the charged particle beam will be 10 times smaller in comparison with the statistical fluctuations than was the case for 100 GFPs total (FIGS. 7 and 8). This can be seen from the qualitative differences between graphs 800 and 1000.

Graphs 900 and 1000 were made with the assumptions listed in Table II. Curve 1006 represents the mean number of photons collected from all the undamaged GFPs in the illuminated area as a function of time into the scan—only the first 0.09 s are shown, during which time eight GFPs are struck and damaged by the charged particle beam (electrons or ions). Each of these damage events is represented by a vertical drop in the signal, such as drop 1012 at the upper left. Above curve 1006 is the +3σ curve 1008 (long dashes), representing expected signal fluctuations three standard deviations above the mean signal level 1006—a relatively unlikely event. Similarly, below curve 1006 is the −3σ curve 1010 (short dashes), representing expected signal fluctuations three standard deviations below the mean signal level 1006—also a relatively unlikely event. The key thing to note here is that at the jump 1012, representing the loss (due to damage) of one GFP, curve 1010 at the left of jump 1012 is now below curve 1008 at the right of jump 1012—this situation differs qualitatively from that shown in FIG. 8 where there was no overlap. Although ±3σ is a fairly stringent criterion, it is clear that distinguishing individual GFP damage events from out of the overall statistical noise in the light signal (such as from detector 360 in FIG. 3) will be more difficult in this case.

TABLE II

Assumptions for Graphs 900 and 1000 in FIGS. 9 and 10.

| | |
|---|---|
| Total Imaging time | 60.00 s |
| Image dimension | 512 # pixels/side |
| Total # pixels | 262144 |
| Pixel time | 228.9 us |
| Laser power at substrate | 0.0030 W = J/s |
| Wavelength | 550.00 nm |
| Energy/photon | 2.25 eV= |
| Incident photons/s | 8.306E+15 /s |
| Diameter of illuminated area | 6.00 um |
| Area of illuminated area | 28.27 um^2 |
| Diameter of GFP | 3.00 nm |
| Area of GFP | 7.07 nm^2 |
| Incident photons/s/GFP | 2.077E+09 /s |
| quantum efficiency estimate | 0.50 |
| collection efficiency estimate | 0.25 |
| photons collected/s/GFP | 2.596E+08 /s/Qdot |
| photons collected/pixel/GFP | 59410.21 |
| statistical fluctuation in #photons/pixel/GFP | 243.74 |
| Number of GFP in illuminated area | 10000 |
| photons collected/pixel time/illum. area | 5.941E+08 |
| statistical fluctuation in #photons/illum. area | 24374.21 |
| Signal/Noise estimate | 2.44 |

Image Processing to Improve FM Localization for Smaller Numbers of FMs

Figure 11:
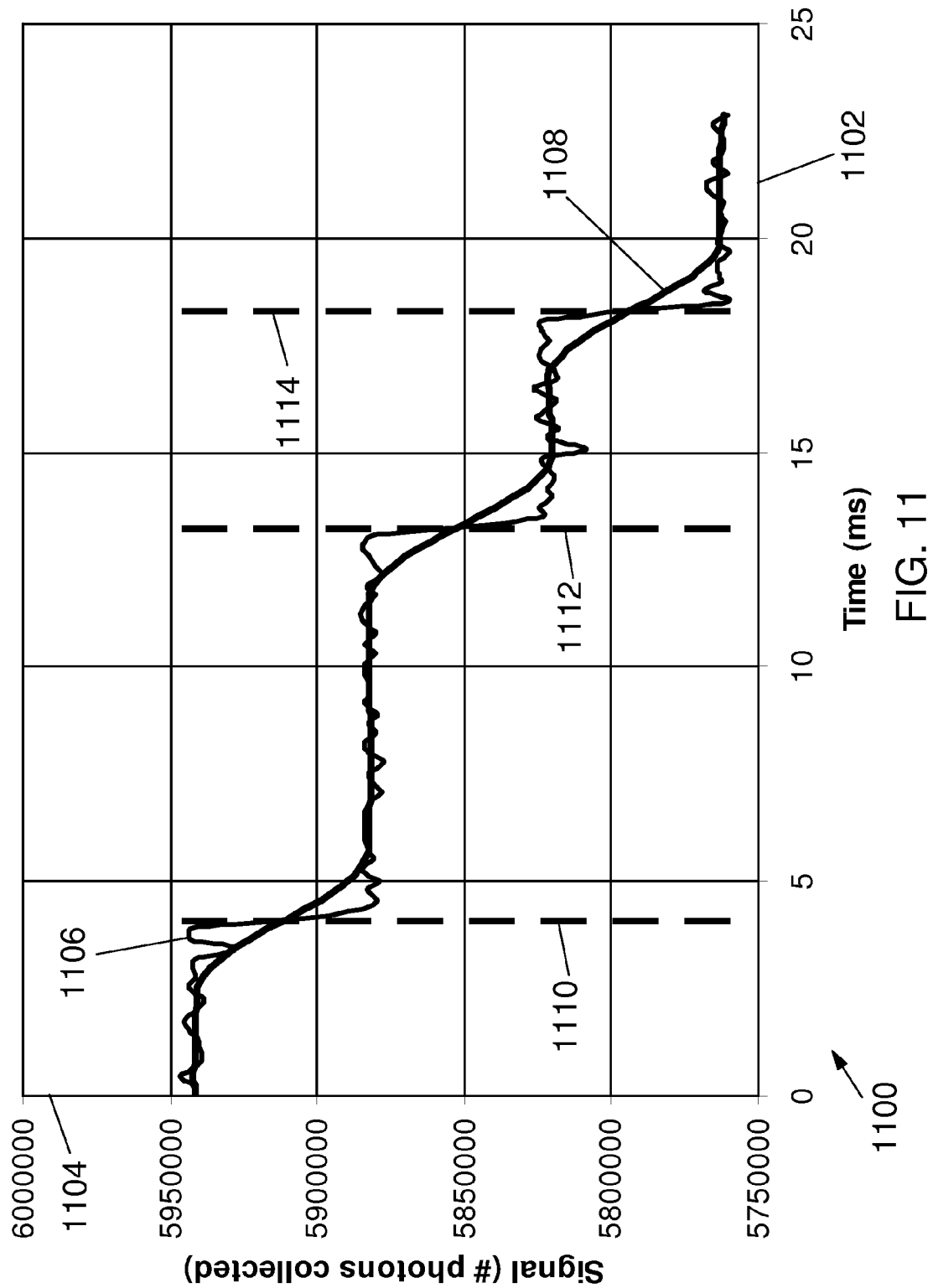
FIG. 11 is a graph showing a raw signal with statistical noise and a smoothed signal as a function of the time during a raster scan, showing damage to the first three GFPs out of a total of 100.
Figure 12:
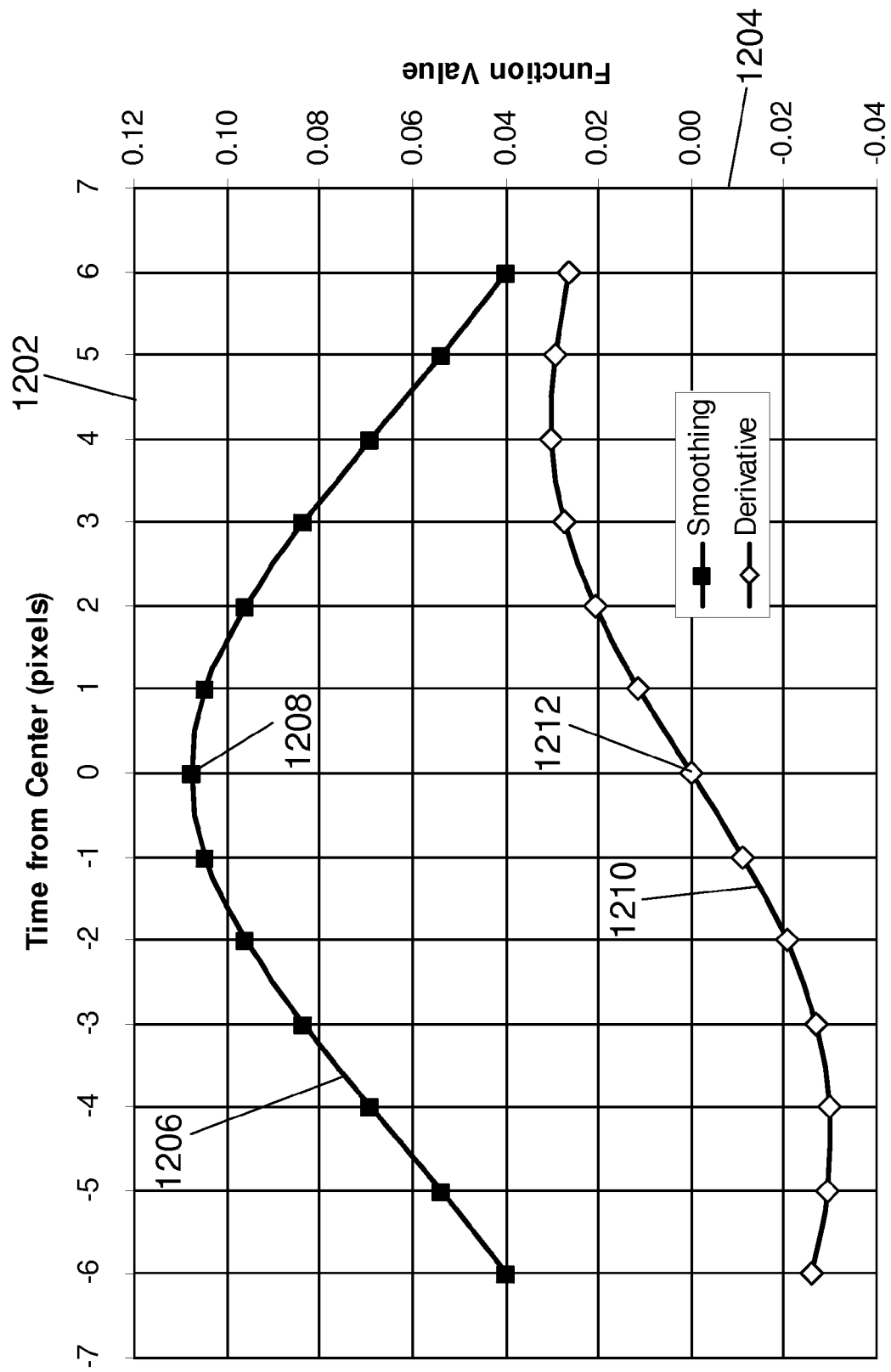
FIG. 12 is a graph showing the smoothing function and the derivative function.
Figure 13:
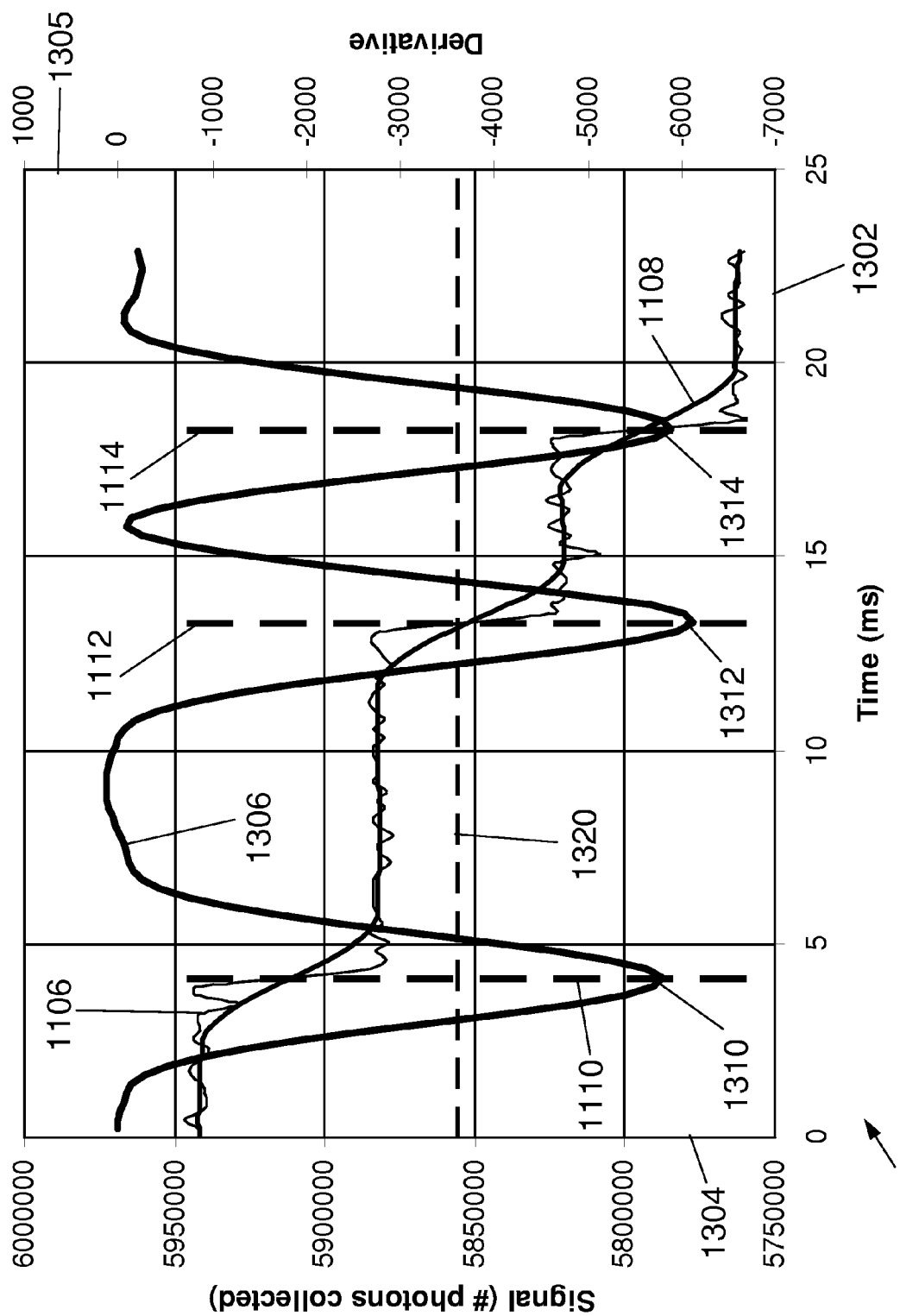
FIG. 13 is a graph showing the raw signal with statistical noise, the smoothed signal, and the smoothed derivative as a function of the time during a raster scan, showing damage to the first three GFPs out of a total of 100.

In this section, we will examine further the localization of fluorescent markers (FMs) such as green fluorescent proteins (GFPs), as first discussed in FIGS. 7 and 8, above, for the case of 100 GFPs in the laser illumination area. FIG. 11 is a graph 1100 showing a raw signal 1106 with statistical noise and a smoothed signal 1108 as a function of the time 1102 during a raster scan, showing damage to the first three GFPs out of the total of 100. Both curves 1106 and 1108 are plotted against a vertical axis 1104 representing the numbers of photons collected from all GFPs per pixel. The noise is assumed to be entirely stochastic, i.e., fluctuations in the signals per pixel will have a standard deviation equal to the square root of the number of photons collected during the pixel time, in this example, 229 μs. With only 100 GFPs being illuminated by the laser, as was discussed for FIG. 8, curves 808 and 810 were close to the mean number of photons curve 806, meaning that for very few pixels will there be enough noise to make it hard to distinguish a GFP damage event. This is further illustrated here, where the small plus and minus signal noise fluctuations cause no problems is locating the GFP damage events at 1110, 1112, and 1114. An image processing method comprising a smoothing step, followed by a differentiation step, is illustrated in FIGS. 11-13. In FIG. 11, curve 1108 is a smoothed version of the raw data curve 1106—the downward steps at each of the three GFP damage events 1110, 1112, and 1114 can clearly be seen. The smoothing function (kernel) 1206 is shown in FIG. 12.

FIG. 12 is a graph 1200 showing a Gaussian smoothing function 1206 centered at 1208 and the derivative function 1210 centered at 1212, plotted against the time 1202 from the center (i.e., the particular pixel data being smoothed) in units of pixels (229 µs dwell time in this example)—the vertical axis 1204 is the values of the two functions (unitless). The sum of the 13 weights (solid squares) in curve 1206 is 1.000, with a maximum value at the center of approximately 0.11. Although in this embodiment, a Gaussian smoothing function 1206 is shown, other smoothing functions are also within the scope of the invention, including, but not limited to, binomial distributions and bell curves. After the raw signal data has been convolved or combined with curve 1206, the resultant smoothed data, such as curve 1108 in FIG. 11, is then autocorrelated with a second, "derivative function" curve 1210, which is the derivative of curve 1206 in this example. Although in this embodiment, curve 1210 is the derivative of a Gaussian curve, other types of "derivative function" curves are possible, including, but not limited to, the derivatives of binomial distributions or bell curves. The full-width half-maximum (FWHM) of Gaussian curve 1206 is a parameter to be optimized, as discussed in FIG. 16, below, and is 10.0 pixels in this example. A simplification of this process would be to first convolve curves 1206 and 1210, which is allowed since both convolution and autocorrelation are associative, and then convolve this resultant curve with the raw image data. Curves 1206 and 1210 are kept separate here to clarify the process.

FIG. 13 is a graph 1300 showing the raw signal 1106 and the smoothed signal 1108 (both from FIG. 11), and the smoothed derivative 1306 as a function of the time 1302 during a raster scan, showing damage to the first three GFPs out of the total of 100. The vertical axis 1304 at the left is for curves 1106 and 1108 in units of photons per pixel from all undamaged GFPs, while the vertical axis 1305 at the right is for the derivative 1306, also in units of the numbers of photons per pixel from all undamaged GFPs. The derivative curve 1306 has three deep downward-going peaks: a first at 1310 corresponding to GFP damage event 1110, a second at 1312 corresponding to GFP damage event 1112, and a third at 1314 corresponding to GFP damage event 1114—note the excellent locational agreement along the time axis. Thus, for small numbers of GFPs being excited by the laser, the image processing routine can easily locate GFP damage events from the raw imaging signal 1106, as shown. The threshold line 1320 defines the maximum height for peaks in the derivative curve 1306 which are counted as GFP damage events. There are thus two parameters in the image processing method of the invention: the FWHM of the smoothing curve (such as curve 1206 in FIG. 12), and the threshold value 1320. Choices for these two parameters are discussed in FIG. 17, below.

Image Processing to Improve FM Localization for Larger Numbers of FMs

Figure 14:
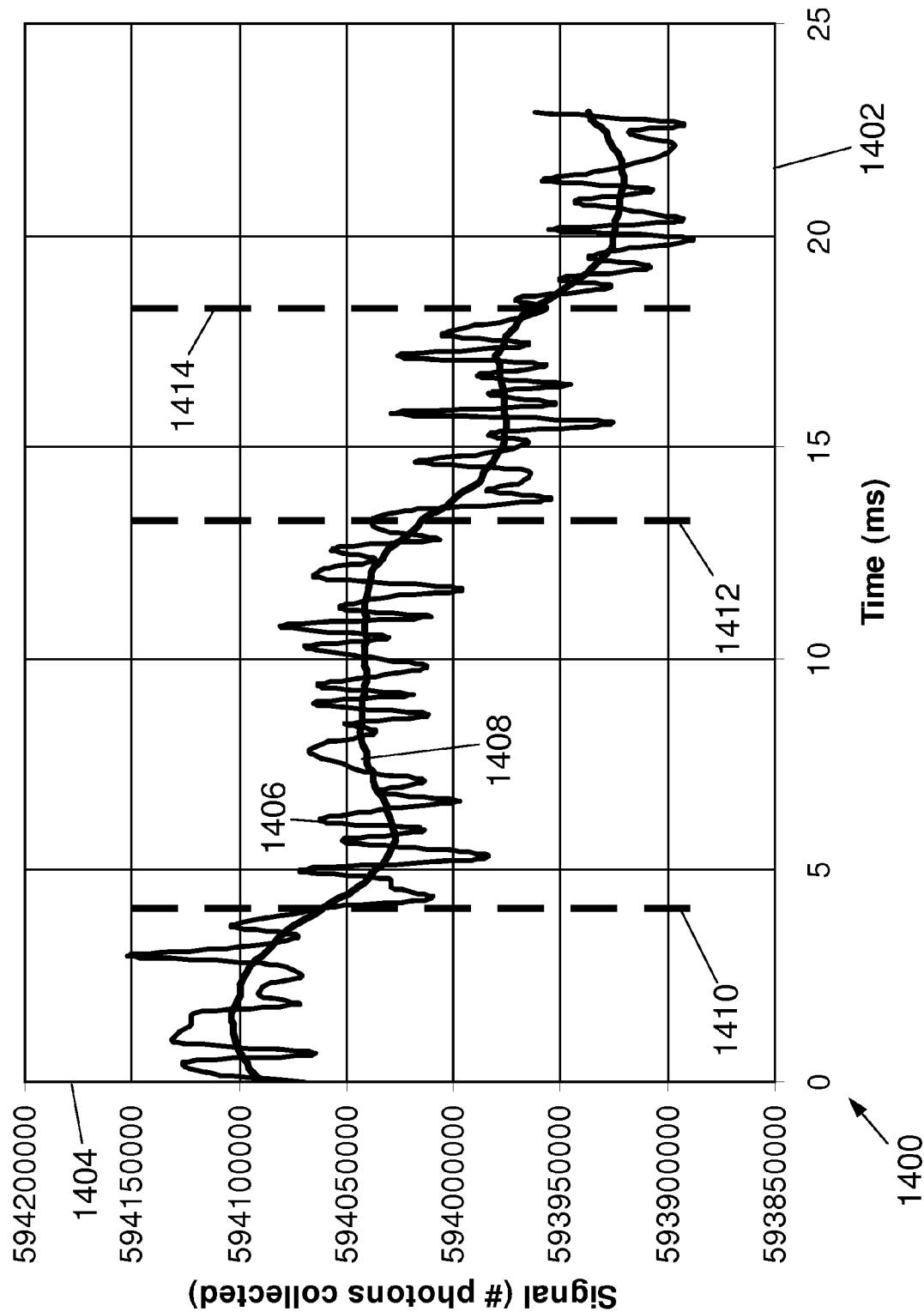
FIG. 14 is a graph showing a raw signal with statistical noise and a smoothed signal as a function of the time during a raster scan, showing damage to the first three GFPs out of a total of 10000.

In this section, we will examine further the localization of fluorescent markers (FMs) such as green fluorescent proteins (GFPs), as first discussed in FIGS. 9 and 10, above, for the case of a hundred times as many GFPs (i.e., now 10000) in the laser illumination area. FIG. 14 for the 10000 GFP case corresponds to FIG. 11 for the 100 GFP case—graph 1400 shows a raw signal 1406 with statistical noise and a smoothed signal 1408 as a function of the time 1402 during a raster scan—showing damage to the first three GFPs out of the total of 10000. Both graphs are plotted against a vertical axis 1404 representing the numbers of photons collected from all undamaged GFPs per pixel. As for the 100 GFP example, the noise is assumed to be entirely stochastic, i.e., fluctuations in the signals per pixel will have a standard deviation equal to the square root of the number of photons collected during the pixel time, in this example, 229 µs. With such a large number of GFPs being illuminated by the laser, as was discussed for FIG. 10, curves 1008 and 1010 were much farther from the mean number of photons curve 1006, meaning that it may potentially be difficult to distinguish individual GFP damage events from the general noise background—for this reason, the image processing method discussed herein was developed. This method is exemplary and is included here to illustrate that, with sufficient image processing of the proper type, the locations of most GFPs, even from a large number within a sample, should be fairly accurate, thus extending the techniques first described in U.S. Pat. No. 7,317,515 to the much higher fluorescent marker densities which may be typical for expressible tags such as GFPs. The same image processing routine illustrated in FIGS. 11-13 was used here. In FIG. 14, curve 1408 is a smoothed version of the raw data curve 1406, calculated using a smoothing curve 1206 having a FWHM of 10.0 pixels—the exact locations of the downward steps at each of the three GFP damage events 1410, 1412, 1414 are difficult to see in the raw data curve 1406. The smoothing function (kernel) 1206 is shown in FIG. 12, generating the smoothed curve 1408, in which the GFP damage events are more apparent.

Figure 15:
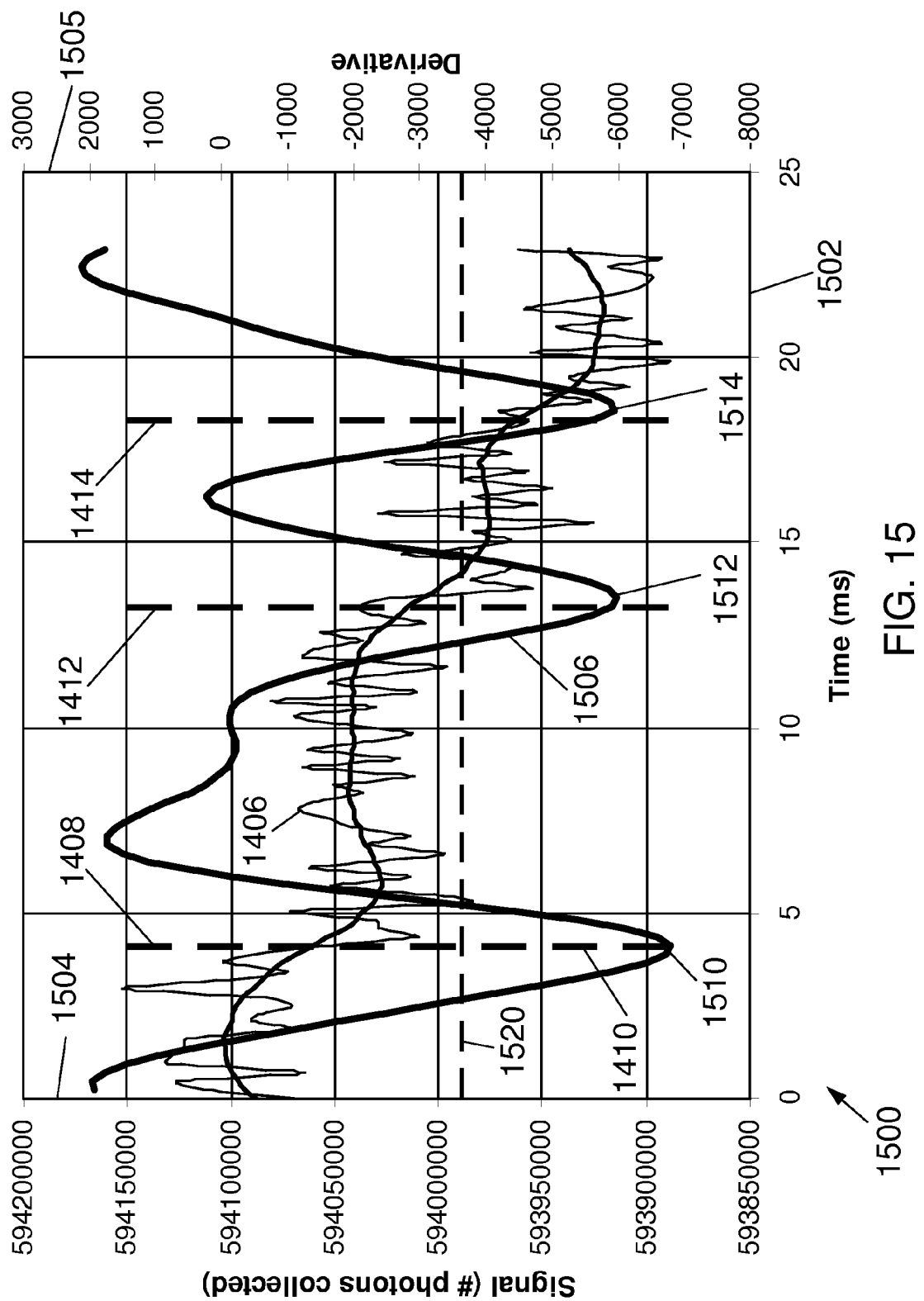
FIG. 15 is a graph showing the raw signal with statistical noise, the smoothed signal, and the smoothed derivative as a function of the time during a raster scan, showing damage to the first three GFPs out of a total of 10000.

FIG. 15 is a graph 1500 showing the raw signal 1406 and the smoothed signal 1408 (both from FIG. 14), and the smoothed derivative 1506 as a function of the time 1502 during a raster scan, showing damage to the first three GFPs out of the total of 10000. The vertical axis 1504 at the left is for curves 1406 and 1408 in units of photons per pixel, while the vertical axis at the right 1505 is for the derivative, also in units of the numbers of photons per pixel. The derivative curve 1506 has three deep downward-going peaks: a first at 1510 corresponding to GFP damage event 1410, a second at 1512 corresponding to GFP damage event 1412, and a third at 1514 corresponding to GFP damage event 1414—note the excellent agreement, in spite of the relatively noisy raw signal data 1406 in this example, compared with curve 1106 in FIG. 11. The threshold line 1520 defines the maximum height for peaks in the derivative curve 1506 which are counted as GFP damage events (compare with threshold 1320 in FIG. 13). There are thus two parameters in the image processing method of the invention for 10000 GFPs, as for 100 GFPs: the FWHM of the smoothing curve (such as curve 1206 in FIG. 12), and the threshold value 1520. Choices for these two parameters are discussed in FIG. 17, below. Thus, for larger numbers of GFPs being illuminated by the laser, the image processing routine can still locate GFP damage events by processing the raw imaging signal 1406, as shown.

Optimization of the Image Processing Method

Figure 16:
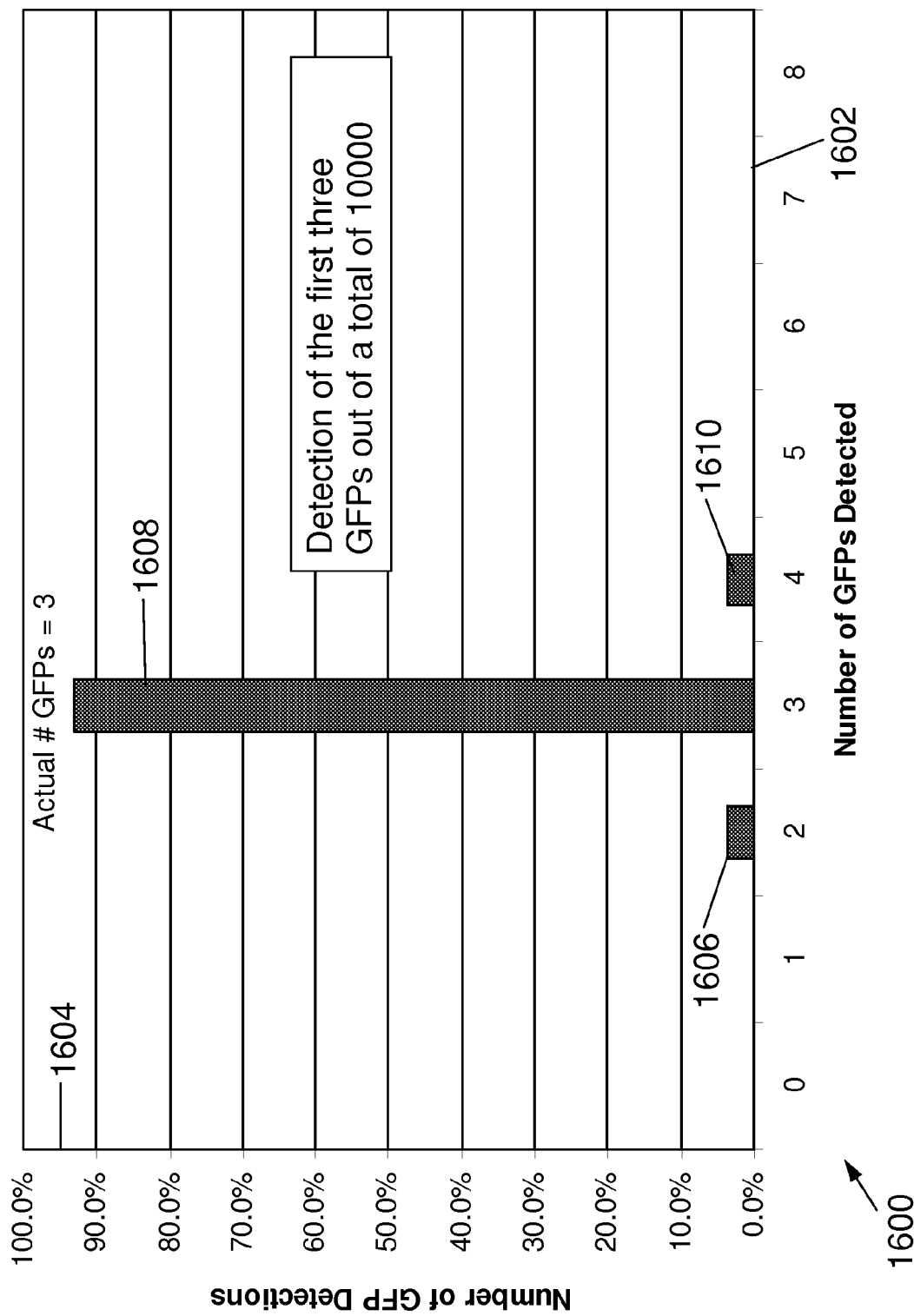
FIG. 16 is a histogram showing the performance of an image processing method for locating GFPs within the scan signal in the presence of large amounts of statistical noise during the detection of the first three GFPs out of a total of 10000 GFPs in the scan field.

We now discuss the optimal choice of FWHM and threshold parameters for the image processing method. This analysis is for exemplary purposes only since it uses simulated noisy data—for actual experimental data, the FWHM and threshold values may be determined empirically from samples with known quantities of FMs (using a regular array of quantum dots or GFPs, for example) by adjusting the FWHM and threshold values to make the detected number of FMs match the actual number of FMs. FIG. 16 is a histogram 1600 showing the performance of an image processing method for locating the first three GFPs in the presence of large amounts of statistical noise and large numbers of GFPs (10000) being illuminated in the scan field. For an example in which there are exactly three GFPs (as in FIGS. 11, 13-15), histogram 1600 shows that for a FWHM of 10.0 pixels and a threshold of −3625, that 94% of the time 1608, the routine will locate exactly the correct number of transitions, with no false positives (i.e., extraneous GFPs) and no false negatives (i.e., no missed GFPs). In 3% of the cases 1606, one out of the three GFPs is missed, while in another 3% of the cases 1610, an extraneous GFP is recorded (3 actual+1 extraneous=4 total).

Figure 17:
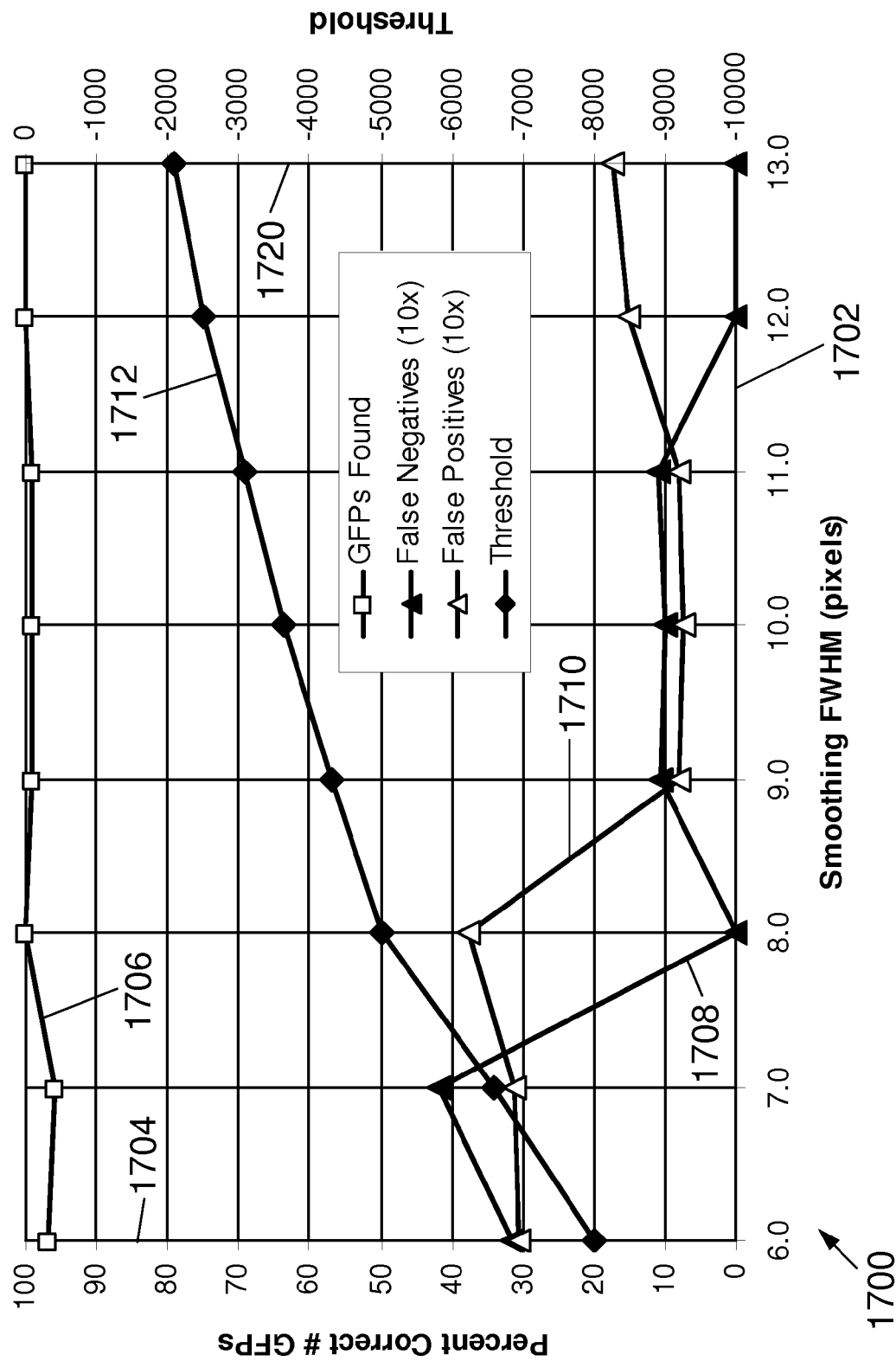
FIG. 17 is a graph of the optimization results for the image processing method.

FIG. 17 is a graph 1700 of the optimization results for the image processing method, illustrating the GFPs found 1706 as a function of the FWHM (in pixels) 1702. The left axis 1704 corresponds to curve 1706 in percent. Curve 1708 illustrates the percentage of false negatives (i.e., the missed GFPs) using axis 1704 magnified by 10×. The sum of curves 1706 and 1708 always equals 100%. Curve 1710 illustrates the percentage of false positives (i.e., extraneous GFP locations not corresponding to real GFPs), also using axis 1704 magnified by 10×. The right axis 1720 corresponds to the curve 1712 of the optimized threshold level for the derivative (i.e., the values for line 1320 in FIG. 13 and line 1520 in FIG. 15). An extensive series of modeling calculations was performed, varying both the FWHM and threshold to determine the optimum values to maximize the level of curve 1706 while reducing and equalizing the percentages of false negatives and false positives. The results are shown in Table III, below. The threshold curve 1712 continues to rise as the FWHM is increased—this is intuitively reasonable, since clearly as the amount of smoothing is increased (with larger FWHM values), the peaks in the derivative will be "blunted" and will not extend as far downwards, requiring smaller thresholds (i.e., higher on the graph) to avoid cutting off those peaks which correspond to actual GFPs.

The four columns in Table III listing the "% of Times Each Number of GFPs Detected" show that in all cases, either two, three or four peaks were detected (never more or less), although in all cases the correct number of peaks was three. When two peaks were detected, it was found that both locations corresponded to actual GFPs, but the peak for the third GFP location did not extend below the threshold and was lost. Thus, for FWHM=6.0 pixels, a 9.50% rate of detection of two peaks corresponds to (9.50%)/3=3.17% rate of false negatives (i.e., missed GFPs), and a (9.50%) ⅔=6.37% rate of correctly detecting GFPs, which adds to the 78.25% rate of detecting the correct number of GFPs (at the correct locations). Similarly, when four peaks were detected, it was found that three locations corresponded to actual GFPs, but an additional peak due to smoothed noise fell below the threshold and was counted as an extraneous GFP. Thus, the 12.25% rate of detecting four peaks corresponds to (12.25%)/4=3.06% rate of false positives, and a (12.25%) ¾=9.19% rate of correctly detecting GFPs, which adds to the 78.25% rate. Thus the total percent of GFPs found correctly is: 3.17%+78.25%+9.19%=96.83%, as shown in Table III.

From this analysis, it appears that a FWHM of 10 pixels with a threshold of −3625 provides a good balance of a minimum number of false positives (0.75%) and false negatives (1.00%), while giving a high rate (99%) of correct GFP localization. In general, it is preferable to use the smallest possible FWHM for smoothing, subject to the constraint of minimizing the error rate, since larger FWHM values may cause the loss of data in the rare cases where GFPs are very close together along the scan line (i.e., only a few pixels apart)—thus a FWHM of 10.0 pixels was chosen, instead of a FWHM of 13.0 pixels which would give the same error rate. Hundreds of simulations with random noise have shown surprising consistency in the results shown in FIG. 17 and Table III. Clearly, the optimum value for the FWHM may be a function of various characteristics of the image. It is expected that this optimization process will be integral to the overall charged particle beam system used to acquire the raw imaging signal and to perform subsequent image processing to produce the final image containing the coordinates of the GFPs in the sample. For actual biological samples, with variations in light emittance from GFPs, and many other issues, theoretical errors rates as demonstrated here are almost certainly more than adequate.

Flowchart of Method for Localizing Expressible Tags Such as GFPs

Figure 18:
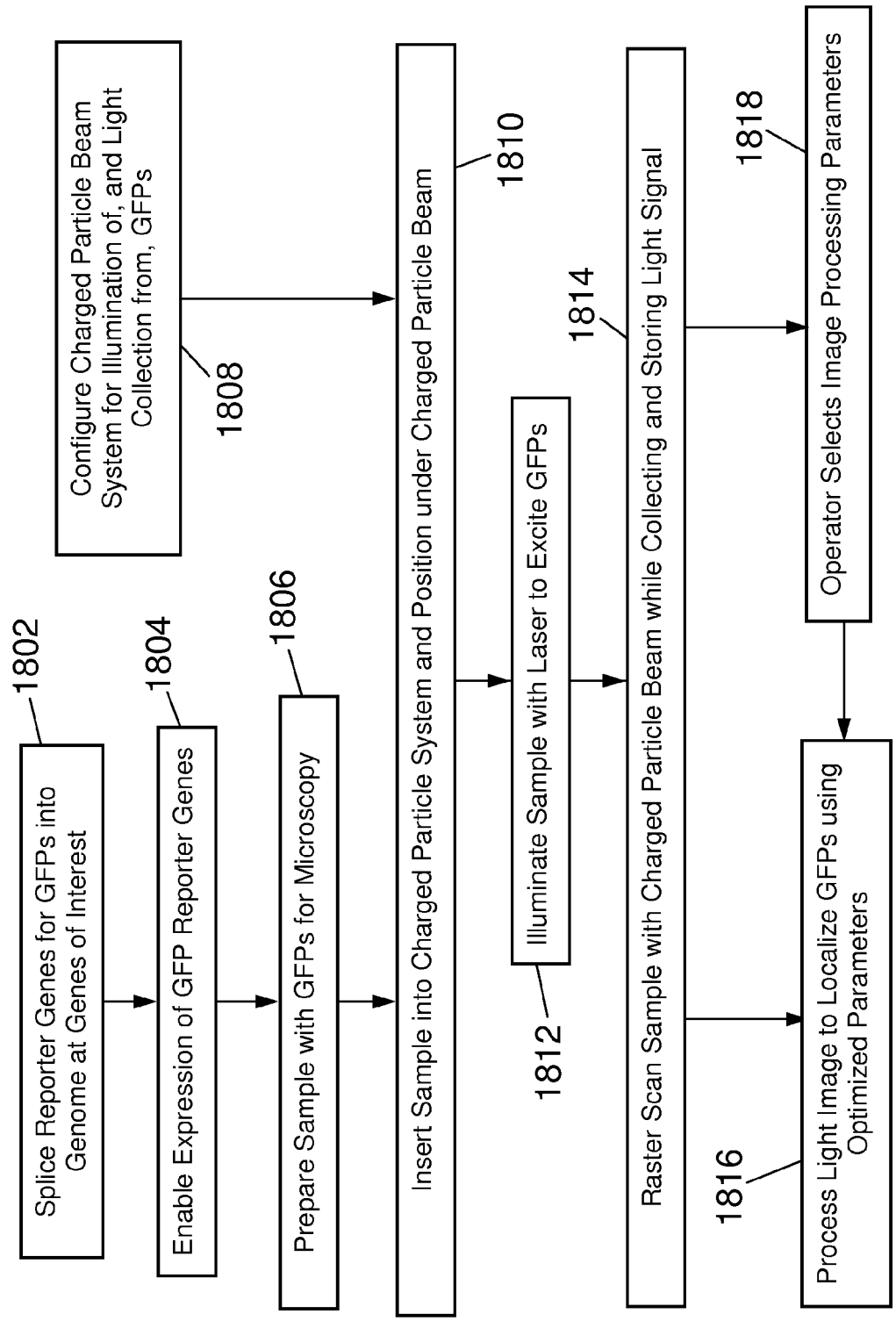
FIG. 18 is a flow chart for the method of the present invention for localizing expressible tags such as GFPs within a sample.

FIG. 18 is a flow chart 1800 for the method of the present invention for localizing expressible tags such as GFPs within a biological sample. In block 1802, the reporter gene for GFP is attached to the regulatory sequence of a particular gene of interest (GoI) in an animal, plant or cell culture which is the subject of research interest, thus whenever the GoI is expressed within the cell (consistent with the cell's need for the protein encoded for by that GoI), the GFP (and the peptide linker, if present) will also be expressed and will remain attached to the protein of interest (PoI). In block 1804, the cell is allowed to express the GFP genes (producing the PoI+linker+GFP amino acid sequence, with the normal secondary, tertiary, and possibly quaternary structures for the PoI). The sample is then prepared for charged particle microscopy in block 1806 in a manner familiar to those skilled in the art—since the GFPs are typical proteins, no special treatment should be necessary to preserve the optical emission properties of the GFPs within the sample. In parallel with blocks 1802-1806, in block 1808, a charged particle beam system is configured for both the laser illumination of the sample (with the required excitation wavelength based on the choice of mutant or wild-type GFP), as well as the efficient collection of emitted fluorescence from the excited GFPs. The three embodiments of the invention illustrated in FIGS. 3, 5 and 6 are exemplary of systems having this required capability, however other systems also having this capability are also possible for implementation of the present invention.

Once the sample has been prepared in block 1806, and the charged particle system has been properly configured in block 1808, the sample can be inserted into the charged particle beam system in block 1810 and positioned under the charged particle beam. The efficient dual imaging capability enabled by the detector optics illustrated in FIGS. 4A and 4B may enable this process to be performed with low levels of damage to the specimen (because imaging doses can be minimized). Now, in block 1812, the sample is illuminated by a laser beam tuned to optimally excite the GFPs within the sample. Preferably almost immediately, rastering of the charged particle beam (comprising either electrons or ions) is started in block 1814 while the light signal from the excited GFPs is collected and stored in an image storage device, such as a frame grabber. Block 1818 represents the operator selecting image processing parameters, such as the FWHM for smoothing and the threshold, as discussed above. This step is optional, and if skipped, block 1816 will use previously-defined image processing parameters. In block 1816, the raw noisy signal data from the sample are processed to determine the locations of GFPs in the sample, and thus the locations of the PoIs encoded for by the GoIs.

Flowchart of Method for Localizing Functionalized Tags Such as Quantum Dots

Figure 19:
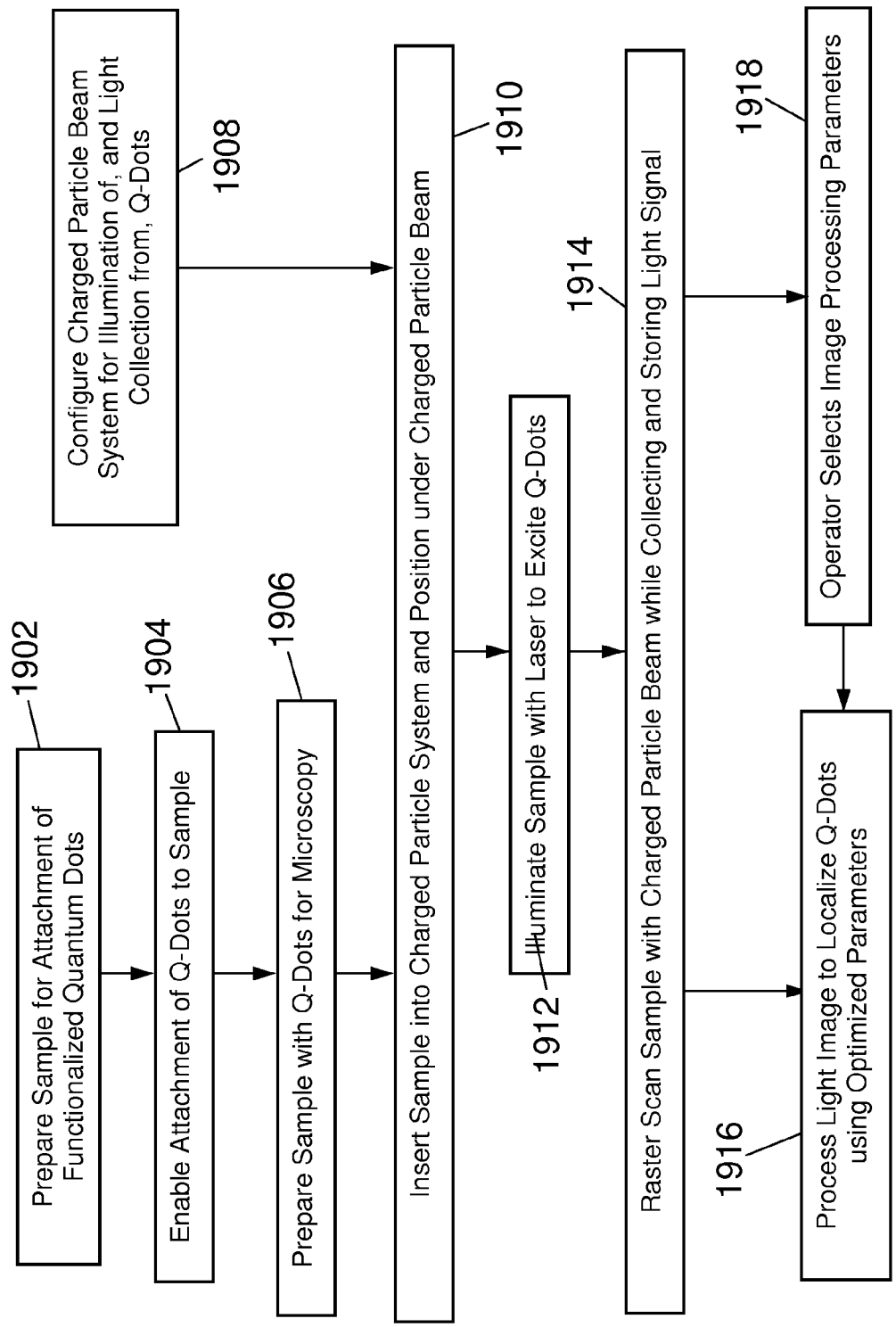
FIG. 19 is a flow chart for the method of the present invention for localizing functionalized tags such as quantum dots within a sample.

FIG. 19 is a flow chart 1900 for the method of the present invention for localizing functionalized tags such as quantum dots within a sample. In block 1902, the sample is prepared for attachment of functionalized quantum dots or other types of functionalized fluorescent markers or dyes to the intracellular components of interest to the researcher. In block 1904, the sample is exposed to a solution of functionalized fluorescent markers (FMs), such as quantum dots (Q-dots). The sample is then prepared for charged particle microscopy in block 1906 in a manner familiar to those skilled in the art. In parallel with blocks 1902-1906, in block 1908, a charged particle beam system is configured for both the laser illumination of the sample [with the required wavelength(s) based on the choice of Q-dot(s)], as well as the efficient collection of emitted fluorescence from the excited Q-dots. The three embodiments of the invention illustrated in FIGS. 3, 5 and 6 are exemplary of systems having this required capability, however other systems also having this capability are also possible for implementation of the present invention.

Once the sample has been prepared in block 1906, and the charged particle system has been properly configured in block 1908, the sample can be inserted into the charged particle beam system in block 1910 and positioned under the charged particle beam. The efficient dual imaging capability enabled by the detector optics illustrated in FIGS. 4A and 4B may enable this process to be performed with low levels of damage to the specimen (because imaging doses can be minimized). Now, in block 1912, the sample is illuminated by a laser beam tuned to optimally excite the Q-dots within the sample. Preferably almost immediately, rastering of the charged particle beam (comprising either electrons or ions) is started in block 1914 while the light signal from the excited Q-dots is collected and stored in an image storage device, such as a frame grabber. Block 1918 represents the operator selecting image processing parameters, such as the FWHM for smoothing and the threshold, as discussed above. This step is optional, and if skipped, block 1916 will use previously-defined image processing parameters. In block 1916, the raw noisy signal data from the sample are processed to determine the locations of Q-dots in the sample, and thus the locations of the PoIs compatible with the Q-dot functionalization.

Combined Secondary Electron and FM Damage Event Imaging

Figure 20:
FIG. 20 is a schematic diagram of a combined secondary electron and fluorescent marker image.

FIG. 20 is a schematic diagram 2000 of a combined secondary electron and fluorescent marker image 2002. During the scanning in a pattern of the charged particle beam across the sample surface by the beam deflector, two images may be simultaneously acquired: a secondary electron (SE) image and a light optical image arising from emitted fluorescent light from the sample containing expressible fluorescent markers (FMs), such as GFPs, or functionalized fluorescent markers, such as Q-dots. The charged particle beam irradiates an area generally somewhat smaller than the area of the light or other radiation beam that causes the FMs to fluoresce—it is preferred that the illumination area not be substantially larger than the area irradiated by the charged particle beam so that the decreases in light collected for each FM damage event may be maximized relative to the overall light background from all the undamaged FMs. The secondary electron image is composed of image pixels, the brightness of each corresponds to the signal from the SE detector while the charged particle beam is on the corresponding point on the sample, the signal from the SE typically being related to the number of SEs detected. Such an image is referred to as a "charged particle beam image" and can be generated by a primary beam of electrons or ions, using detected secondary electrons, backscattered electrons, secondary ions, or other types of signal. In FIG. 20, the SE image corresponds to the various lines 2008, circles 2006, ovals, and shaded areas 2004, corresponding to various intracellular components of the cell being imaged, e.g., nuclei, cell membranes, smooth and rough endoplasmic reticula, mitochodria, vesicles, etc. Superimposed on the SE image are indicators of the locations of the multiplicity of FMs, indicated by small black circles in the figure. As the charged particle beam is scanned across the sample, the position of the charged particle beam is registered at the instant that a reduction or extinguishment of fluorescence of a FM is detected. The extinguishment is determined by the image processing method in FIG. 21—these data are stored in the FM Location File generated by block 2122 of FIG. 21. The benefits of the high collection efficiency combined SE and light detection enabled by the detector optics illustrated in FIGS. 4A and 4B are apparent here—high SE collection efficiency improves the image quality of the various intracellular structures, while the efficient collection of light from the sample enables a high percentage of the FMs in the sample to be precisely located, with the location being stored and superimposed onto the SE image. Since the SE and light data both arise from the same raster scan, superposition of the FM locations on the SE image can be very precise. Alternatively, the locations of FMs within the sample can be superimposed on typical TEM images (elastic, inelastic, energy-filtered inelastic, etc.) created using signals from detector 586 in FIG. 5, or detector 686 in FIG. 6.

Exemplary Image Processing Method

Figure 21:
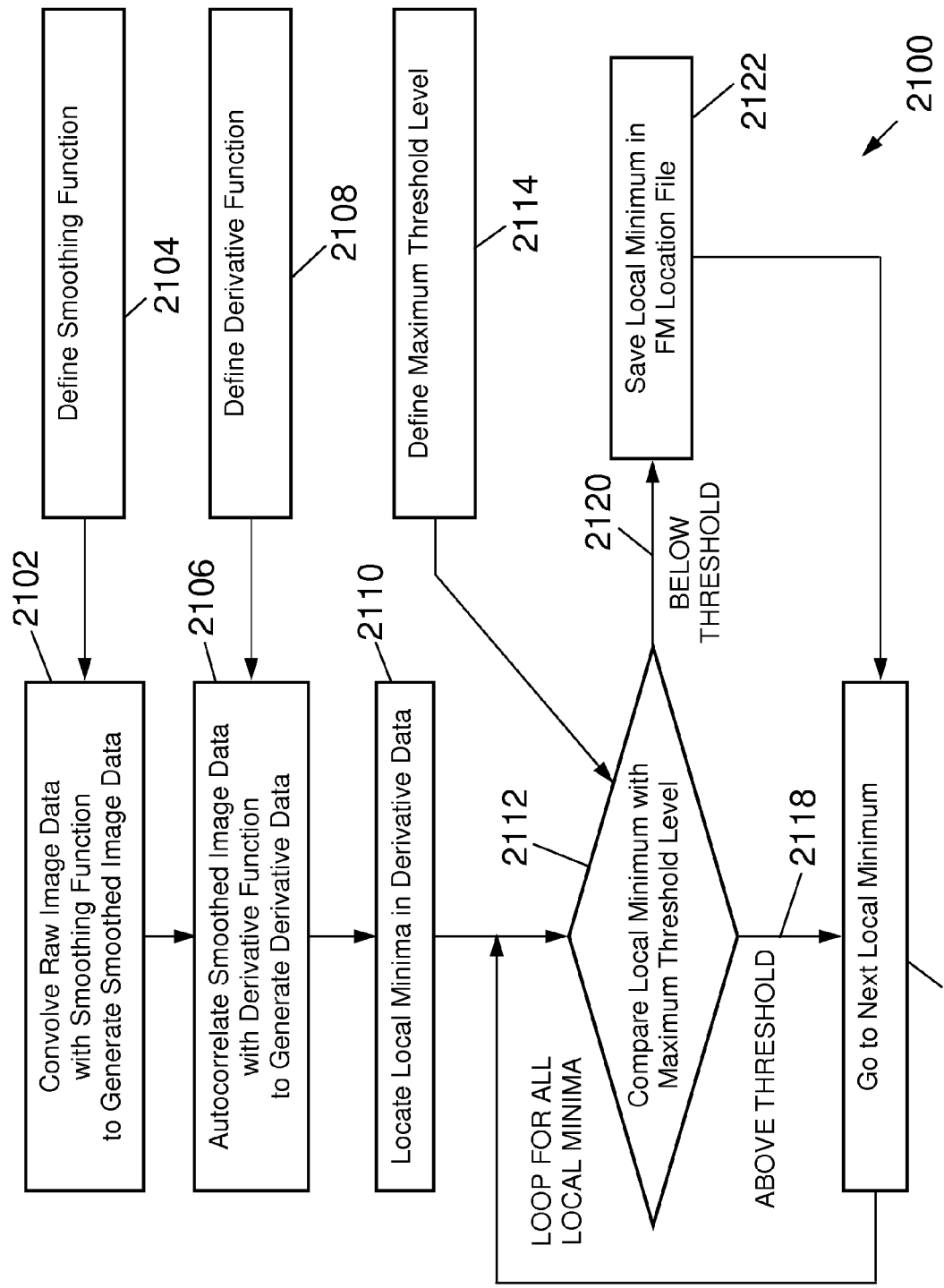
FIG. 21 is a flow chart for an image processing method for localizing fluorescent markers.

FIG. 21 is a flow chart 2100 for an image processing method for localizing fluorescent markers (FMs) within a sample. This method assumes that a full raster scan of the sample by the charged particle beam has been completed—during this scan, a set of raw image data for the set of pixels comprising the raster has been acquired and stored in a first image memory. Each pixel datum is a number proportional to the emitted fluorescent light intensity from all the undamaged fluorescent markers (FMs), such as GFPs or Q-dots, in the sample averaged over the pixel dwell time. An image processor may be comprised in the system controller such as 362, 562, and 662 in FIGS. 3, 5, and 6, respectively. Alternatively, an image processor may be comprised in a separate off-line processing computer (not shown). In block 2102, the image processor convolves the raw image data (such as curve 1106 in FIG. 11, or curve 1406 in FIG. 14) with a pre-determined smoothing function from block 2104 (such as curve 1206 in FIG. 12) to generate smoothed image data which is stored in a second image memory. In block 2106, the smoothed image data (such as curve 1108 in FIG. 11, or curve 1408 in FIG. 14) from block 2102 is autocorrelated with a pre-determined derivative function from block 2108 (such as curve 1210 in FIG. 12) to generate derivative data which is stored in a third image memory.

Next, in block 2110, the image processor scans the derivative data for all local minima—both the values and locations of all local minima are stored in a Derivative Minimum Location File (DMLF). Examples of local minima include peaks 1310, 1312, and 1314 in FIG. 13, or peaks 1510, 1512, and 1514 in FIG. 15. A loop comprising decision block 2112 and blocks 2114, 2122, and 2124 is then executed for each of the local minima in the DMLF. The value of each local minimum is compared with a predetermined maximum threshold level from block 2114, such as level 1320 in FIG. 13, or level 1520 in FIG. 15. In general, many of the local minima will correspond to random noise fluctuations in the data, and not to true locations of FMs in the sample—with the proper selection of the maximum threshold level in block 2114, most of the local minima which do not correspond to actual FMs will be eliminated by decision block 2112 (thereby reducing the number of false positives). Also, it is preferred that most of the local minima which do correspond to actual FMs will fall below the maximum threshold level (thereby reducing the number of false negatives). The success of the image processing method in localizing a large fraction of actual FMs, while excluding a large fraction of minima not corresponding to actual FMs relies on the fact that when an actual FM is damaged, there is a permanent reduction in the light from the sample, while for random noise the light from the sample goes up and down, but remains the same on average. Thus, by smoothing the data and using a derivative function, the up and down fluctuations due to noise will be smoothed out, while step reductions in light from the sample will still be detectable. Path 2120 from decision block 2112 corresponds to all local minima falling below the maximum threshold level—the locations of these local minima are saved in the FM Location File (FMLF) in block 2122, and the loop then proceeds to block 2124. All local minima having values above the maximum threshold level follow path 2118 to block 2124 and are not stored in the FMLF since these data are, by definition, assumed not to correspond to actual FM locations (this is the purpose of the threshold). In block 2124, the loop increments to the next local minimum in the DMLF until all stored local minima have been analyzed in decision block 2112. At the conclusion of the image processing method, the FMLF will preferably contain the locations of the majority of the FMs within the sample, and a minimum number of extraneous (non FM) locations—thus the levels of false negatives (missed FMs) and false positives (erroneous extra FMs) will both be minimized, as discussed in FIGS. 16 and 17.

The above discussion has used the term "green fluorescent protein", or "GFP", to represent any type of expressible biological fluorescent marker, or tag, all being within the scope of the invention. The term "Q-dot" has been used to represent any type of functionalized fluorescent marker as commonly used in the art, all being within the scope of the invention. Although three embodiments of charged particle systems for implementing the present invention are presented, it is understood that other system configurations are also possible within the scope if the invention. The term secondary electron may include not only low energy secondary electrons, but also Auger electrons and backscattered electrons.

TABLE III

Image Processing Routine Optimization Results. For each set of FWHM and threshold values, 300 simulation runs (each with exactly three initial GFP damage events) were run to get good statistics on the performance of the image processing routine.

| FWHM | | % of Times Each No. of GFPs Detected | | | | GFPs Found | False Neg. | False Pos. |
|---|---|---|---|---|---|---|---|---|
| (pixels) | Threshold | 2.0 | 3.0 | 4.0 | 5.0 | (%) | (%) | (%) |
| 6.0 | −8000 | 9.50 | 78.25 | 12.25 | 0.00 | 96.83 | 3.17 | 3.06 |
| 7.0 | −6600 | 12.50 | 75.00 | 12.5 | 0.00 | 95.83 | 4.17 | 3.13 |
| 8.0 | −5000 | 0.00 | 85.00 | 15.00 | 0.00 | 100.00 | 0.00 | 3.75 |
| 9.0 | −4300 | 3.17 | 93.67 | 3.17 | 0.00 | 98.94 | 1.06 | 0.79 |
| 10.0 | −3625 | 3.00 | 94.00 | 3.00 | 0.00 | 99.00 | 1.00 | 0.75 |
| 11.0 | −3100 | 3.25 | 93.50 | 3.25 | 0.00 | 98.92 | 1.08 | 0.81 |
| 12.0 | −2500 | 0.00 | 94.00 | 6.00 | 0.00 | 100.00 | 0.00 | 1.50 |
| 13.0 | −2100 | 0.00 | 93.00 | 7.00 | 0.00 | 100.00 | 0.00 | 1.75 |

Computer programs can be applied to input data to perform the functions described herein and thereby transform the input data to generate output data. The output information is applied to one or more output devices such as a display monitor. In preferred embodiments of the present invention, the transformed data represents physical and tangible objects, including producing a particular visual depiction of the physical and tangible objects on a display.

Preferred embodiments of the present invention also make use of a particle beam apparatus, such as a FIB or SEM, in order to image a sample using a beam of particles. Such particles used to image a sample inherently interact with the sample resulting in some degree of physical transformation. Further, throughout the present specification, discussions utilizing terms such as "calculating," "determining," "measuring," "generating," "detecting," "forming," or the like, also refer to the action and processes of a computer system, or similar electronic device, that manipulates and transforms data represented as physical quantities within the computer system into other data similarly represented as physical quantities within the computer system or other information storage, transmission or display devices.

Although embodiments of the present invention and their advantages have been described in detail, it should be understood that various changes, substitutions and alterations can be made to the embodiments described herein without departing from the spirit and scope of the invention as defined by the appended claims. The invention includes several novel and inventive aspects which may be used together or separately in different embodiments. Moreover, the scope of the present application is not intended to be limited to the particular embodiments of the process, machine, manufacture, composition of matter, means, methods and steps described in the specification. For example, the novel image processing method can be used with other types of systems, including prior art systems and yet-to-be developed systems. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A charged particle system, comprising:
   a charged particle optical column for directing a charged particle beam onto a sample;
   a secondary electron detector for collecting secondary electrons emitted from the sample upon impact of the charged particle beam;
   a light detector for detecting light emitted by the sample; and
   an electrically conductive mirror, the mirror configured to:
   reflect toward the light detector the light emitted from the sample; and
   provide an electric field to deflect the secondary electrons from the sample into the secondary electron detector.

2. The system of claim 1 in which the mirror is a paraboloidal mirror for collecting light from an area of the sample, the focal point being in proximity to the impact point of the charged particle beam.

3. The system of claim 1 in which the light detector detects light emitted by the impact of the charged particle beam on the sample.

4. The system of claim 1, further comprising a beam splitter located between the mirror and the light detector; the beam splitter being configured to:
   transmit the light reflected by the mirror into the light detector; and
   reflect the light from a light source towards the mirror.

5. The system of claim 4, further comprising a color filter located between the beam splitter and the light detector, the transmissivity of the color filter being adjusted to largely block transmission of light from the light source, while passing light emitted by the sample.

6. The system of claim 1 in which the solid collection angle for both light emitted from the sample and for secondary electrons is greater than $\pi/2$ steradians.

7. The system of claim 1 in which the light detector comprises a multiplicity of detectors, each detector in the multiplicity of detectors being configured to collect light of a different frequency.

8. The system of claim 1 in which the light detector and mirror are positioned above the sample, and further comprising:
- a transmitted electron detector located below the sample;
- a second light detector for detecting light emitted by sample; and
- a second mirror positioned between the sample and the transmitted electron detector, the second mirror having a focal point positioned in proximity to the impact point of the charged particle beam with the sample, the second mirror being configured to reflect the light emitted by the sample toward the second light detector.

9. A charged particle system, comprising:
- a charged particle beam source for generating charged particles;
- a charged particle beam optical column for focusing a beam of charged particles from the charged particle beam source onto a sample;
- a sample stage for holding a sample in a sample position, a sample plane through the sample position dividing space into a region above the sample plane including the charged particle beam source and a region below the sample plane;
- a secondary electron detector for collecting secondary electrons emitted from the sample due to the impact of the charged particle beam with the sample, the secondary electron detector positioned above the sample plane;
- a light detector for detecting light emitted by the sample upon impact of the charged particle beam; and
- an electrically conductive mirror positioned above the sample plane, the mirror configured to deflect light emitted by the sample onto the light detector without the light passing completely through the sample, and to deflect secondary particles from the sample.

10. The charged particle beam system of claim 9 in which the mirror comprises an electrically conductive paraboloidal mirror.

11. The charged particle beam system of claim 10 in which the mirror has a focal point for light, the focal point positioned in proximity to the impact point of the charged particle beam with the sample.

12. The charged particle beam system of claim 11 in which the mirror is configured to reflect the light emitted by the sample toward a light detector.

13. The charged particle beam system of claim 10 further comprising an electrode having a hole through which the charged particle beam passes and configured to provide an electric field between the electrode and the electrically conductive paraboloidal mirror configurable to deflect the secondary electrons from the sample into the secondary electron detector.

14. The charged particle beam system of claim 13 in which the electrode is biased to approximately the potential of the sample.

15. A method for examining a sample, comprising the steps of:
- directing a charged particle beam in a pattern onto the sample surface, the charged particle impacting the sample in a region;
- detecting light emitted from the region, the light from the sample being reflected by an electrically conductive first mirror toward a detector, the first mirror having an opening therein for passage of the charged particle beam;
- moving the charged particle beam across the surface of the sample in a pattern;
- deflecting away from the first mirror and towards the detector charged particles from the sample caused by the impact of the charged particle beam on the sample; and
- determining from the detected light the composition of the sample.

16. The method of claim 15 in which the charged particle beam comprises an electron beam or a focused ion beam.

17. The method of claim 15 in which the charged particle detector is positioned on the same side of the sample as the mirror and below the level of the mirror.

18. The method of claim 15 in which deflecting away from the first mirror and towards the detector charged particles from the sample comprises providing an electrical bias on the mirror.

19. The method of claim 15 in which the light emitted from the sample is collected by a second mirror on the opposite side of the sample from the first mirror.

\* \* \* \* \*